United States Patent [19]
Hodges et al.

[11] Patent Number: 6,012,926
[45] Date of Patent: *Jan. 11, 2000

[54] VIRTUAL REALITY SYSTEM FOR TREATING PATIENTS WITH ANXIETY DISORDERS

[75] Inventors: Larry F. Hodges, Lithonia; Barbara O. Rothbaum, Atlanta, both of Ga.

[73] Assignees: Emory University; Georgia Institute of Technology, both of Atlanta, Ga.

[*] Notice: This patent is subject to a terminal disclaimer.

[21] Appl. No.: 08/906,016

[22] Filed: Aug. 4, 1997

Related U.S. Application Data

[63] Continuation-in-part of application No. 08/622,756, Mar. 27, 1996, Pat. No. 5,807,114.

[51] Int. Cl.$^7$ ............................. G09B 19/00; G09B 9/02; G09B 9/08
[52] U.S. Cl. ............................. 434/236; 434/29; 434/38; 434/46; 434/48; 434/59
[58] Field of Search ................................ 434/236, 29, 30, 434/35, 36, 38, 41, 43, 44, 46, 48–51, 55, 59, 69, 219, 220, 226, 307 R, 308, 309, 310, 314, 322–324; 472/59, 60, 61, 64, 65, 68; 364/578

[56] References Cited

U.S. PATENT DOCUMENTS

| | | | |
|---|---|---|---|
| 4,683,891 | 8/1987 | Cornellier et al. | 128/630 |
| 5,316,480 | 5/1994 | Ellsworth | 434/29 |
| 5,320,538 | 6/1994 | Baum | 434/307 |
| 5,447,166 | 9/1995 | Gevins | 128/731 |
| 5,469,511 | 11/1995 | Lewis et al. | 381/173 |
| 5,601,435 | 2/1997 | Quy | 434/307 |
| 5,807,114 | 9/1998 | Hodges et al. | 434/236 |

OTHER PUBLICATIONS

Exertainment, "The Interactive Workout that Makes Exercise Time Fly!", Life Fitness Corp., 1994.
"Curing Acrophobia", Discovery Channel Online, Cyberlife, The Digital Culture, Show #1202, Jun. 18, 1996.
Stevens, J.E., Flights Into Virtual Reality Treating Real World Disorders, The Washington Post, Mar. 27, 1995, Science Psychology.
Virtually Present, Treatment of Acrophobia by Using Virtual Reality Graded Exposure, R. Kooper, Aug. 19, 1994, Delft University of Technology, Computer Science, Department of Information Systems.
Virtual Environments Research at the Georgia Tech GVC Center, by Larry F. Hodges, et al., Presence, vol. 2, No. 3, Summer 1993, 234–243.
Virtual Reality Graded Exposure in the Treatment of Acrophobia: A Case Report, B. Rothbaum et al., Fall 1995, Behavior Terapy, vol. 26, 547–554.

(List continued on next page.)

Primary Examiner—Robert A. Hafer
Assistant Examiner—John Edmund Rovnak
Attorney, Agent, or Firm—Troutman Sanders LLP; Joel S. Goldman

[57] ABSTRACT

A virtual reality system provides effective exposure treatment for psychiatric patients suffering from a particular anxiety disorder. The system is characterized by a video screen disposed in front of the patient to display an image of a specific graphical environment that is intended to trigger anxiety within the patient as a result of the particular patient phobia. A headset is worn by the patient, and has sensors disposed to detect movement and positioning of the patient's head. A computer program controls the operation of the system, and is designed to control the display of the graphical environment on the video screen, monitor the headset sensors and determine the position of the patient's head, and controllably manipulate the graphical environment displayed on the video screen to reflect the movement and position of the patient's head. In a preferred embodiment, a sensor is provided to automatically detect a level of patient anxiety, and the computer program is designed to monitor this sensor and controllably manipulate the graphical environment displayed on the video screen in response thereto. In other embodiments, sound and tactile feedback are provided to further enhance the graphic emulation.

18 Claims, 15 Drawing Sheets

OTHER PUBLICATIONS

Effectiveness of Computer–Generated (Virtually Reality) Graded Exposure in the Treatment of Acrophobia, B. Rothbaum, et al., Apr. 1995, Am. J. Psychiatry, 152:4, 626–628.

Virtual Enviroments for Treating the Fear of Heights, L. Hodges, et al., Jul. 1995, IEEE, 27–34.

Virtual Reality Exposure Therapy in the Treatment of Fear of Flying: A Case Report, B. Rothbaum, et al., May–Jun. 1996, Behav. Res. Ther. 34:5/6, 477–491.

Virtual Reality Exposure Therapy, B. Rothbaum, et al., Summer 1997, J. Psychotherapy Practice and Res., 6:219–226.

VIRTUAL REALITY SYSTEM FOR TREATING PATIENTS WITH ANXIETY DISORDERS

CROSS REFERENCE TO RELATED APPLICATION

This application is a Continuation-In-Part of U.S. patent application Ser. No. 08/622,756 filed Mar. 27, 1996, U.S. Pat. No. 5,807,114.

BACKGROUND OF THE INVENTION

1. Field of the Invention

The present invention generally relates to psychiatric treatment of patients with phobias, and more particularly to a system for providing exposure therapy for psychiatric treatment of patients having various phobias.

2. Discussion of the Related Art

As is well known, people from all walks of life are known to suffer from a wide variety of phobias or related anxiety disorders. Simply defined, a phobia is an irrational fear of an object, activity, or situation that leads to a compelling desire to avoid it—e.g., fear of heights. Not only are there a wide variety of phobias, but any given type may manifest itself differently, or to a different degree, in different persons. Therefore, treatment programs are generally tailored individually to specific patients. Nevertheless, certain generalities in regard to treatment programs can be made.

Namely, exposure theory espouses the view that patients suffering from a particular phobia can be treated to successfully manage that phobia by repeated exposure to the particular situation. For example, patients suffering from acrophobia (fear of heights) may be treated by exposure to high places. Elevators, balconies, building windows, bridges, and airplanes are environments where a patient being treated for acrophobia may be deployed. Although the degree of success varies from patient to patient, exposure therapy has been proven effective in many cases and controlled studies.

A more particular derivation of exposure therapy is referred to as "graded exposure therapy", whereby a patient is exposed to particular situations in gradations of gradual but increasing severity. For example, an acrophobic patient may be treated by leading the person to a first floor balcony. While the initial deployment may result in relatively high levels of anxiety, it has been found that the anxiety level will typically subside after a patient has spent some period of time in the environment. Therefore, after the patient has spent some time on the first floor balcony, and has reached some level of comfort in that position, he may then be led to a second floor balcony, and so on. In this way, the patient may be continually moved to higher and higher elevations, allowing the anxiety level to subside at each level before continuing. Repeated sessions of treatment in this manner (i.e., graded exposure) have been found to successfully help patients in facing and managing phobias. It is, moreover, desired to vary the treatment environment. In one session, a patient may be gradually led to successive balcony floors as described above. In a subsequent session, that same patient may be led up multiple flights of stairs, elevated up several floors in an elevator, or exposed to some other environment.

Typically, there are two categories or methods by which exposure therapy is practiced in vivo and imaginal. Pursuant to the in vivo (i.e., "real life") approach, patients are exposed to real situations and stimuli. In contrast, the imaginal method is practiced by having patients imagine particular situations or scenarios. For example, in a treatment method known as systematic desensitization, a patient is instructed to relax, then imagine a stimuli for a situation that causes anxiety, relax again, then stop imagining. These steps are repeated and as the levels of patient anxiety begin to subside, the patient is asked to imagine a different scenario that provokes higher levels of anxiety.

While both in vivo and imaginal therapy has proven effective for treating different patients, both are characterized by various shortcomings. Notably, in vivo treatment is typically time consuming and therefore costly. In this approach, the patient must be taken from the therapist's office and deployed in real life settings, which excessively consumes the therapist's time and is therefore costly. In addition, subjecting the patient to situations outside the office (e.g., public places) compromises the doctor patient confidentiality and may be embarrassing for the patient. As a result, many patients are unwilling to undergo such therapy and go untreated. Moreover, in certain treatment environments such as an elevator or an airplane, the environment is not under patient or therapist control, often resulting in excessive levels of anxiety on the part of the patient, which may be counter-productive for the therapy.

Likewise, the imaginal method of treatment suffers from shortcomings of its own. Most notably, this method has proven to be largely ineffective for patients with very poor imaginations. Like the in vivo method, the imaginal method is often time consuming and expensive, as it may take excessive amounts of time for the patients to imagine scenarios to adequately invoke episodes of anxiety for proper treatment. In addition, patients may find it often difficult to sustain the imagined scenario once high levels of anxiety have set in.

Although the specific examples set forth above detail scenarios and environments for treating acrophobic patients, it is appreciated that exposure therapy has been widely used in a variety of phobias and anxiety disorders.

SUMMARY OF THE INVENTION

Accordingly, a primary object of the present invention is to provide an improved system and method for treating patients using exposure therapy.

A more specific object of the present invention is to provide a system for effecting exposure therapy on patients within the confines of a doctor's office.

Another object of the present invention is to provide a system for effecting exposure therapy in a timely and therefore cost-effective manner.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, the present invention is generally directed to a virtual reality system for treating patients with a particular anxiety disorder. Principally, the system includes a video screen for displaying a graphical environment, a headset worn by the patient and having sensors disposed to detect movement and positioning of the patient's head, and a computer program for controlling the operation of the system. More particularly, the computer program controls the graphical display on the video screen, so as to present a particular graphical environment that is targeted for a particular patient feared stimulus to elicit responsive anxiety from that patient. As is known in virtual reality systems, the computer program monitors the sensors associated with the headset to determine the position and movement of the patient's head. In response, the program controls the graphical display on the video screen accordingly.

In accordance with one aspect of the present invention, means are provided for sensing or detecting patient anxiety. This feature may be provided by a sensor that monitors the patients pulse rate or alternatively blood pressure, whereby increasing pulse rate or blood pressure indicates increasing levels of anxiety. Alternatively, an electrodermal (or galvanic skin response) sensor may be provided to monitor perspiration levels of the patient, whereby increased perspiration indicates increased anxiety. In yet another embodiment, the therapist may monitor the patient's anxiety, either by observing visible indications, or by talking with the patient and being told when the patient is uncomfortably anxious using the Subjective Units of Discomfort (SUDS) anxiety scale. A separate video screen may be provided for the therapist to monitor, so that the therapist can better control the emulated environment. For example, one virtual environment presents an elevator for treating acrophobic patients. By visually monitoring the graphical environment presented to the patient, the therapist can better control the movement and height of the "virtual" elevator, using the patient's anxiety level to guide the height of the elevator.

In accordance with another aspect of invention, tactile feedback is provided to further enhance the "virtual" environment. In this regard, physical objects may be statically displayed within the reach of the patient, that correspond in placement with visible objects displayed on the video screen. Patients may, therefore, touch objects that are displayed in the image to further enhance the effect of the virtual scene. Alternatively, sound or vibratory feedback may be provided. In one embodiment of the present invention, the interior of an aircraft, including a view from a window, is graphically displayed on the video screen for treating patients who have a fear of flying. Sound corresponding to aircraft engine noise may be provided to enhance the visible scene. In addition, the patient may view this scene from a seated position to emulate a seat on the aircraft. The seat may, correspondingly, be vibrated in accordance with sound vibrations and graphic perturbations (indicative of the aircraft having a bumpy ride). This too reinforces the virtual environment presented to the patient, and enhances the results of the therapy session.

In accordance with a related aspect of the present invention, the sound generated and directed to the patient may be controllably affected by movement of the patient's head. Just as the computer program is designed to monitor a headset worn by the patient to controllably manipulate the graphical image displayed on the video screen, the program may likewise control the presentation of sound to the patient. Therefore, not only will the sound be varied in a corresponding relation to the changing scene displayed on the video screen, but it may also be varied (in volume and direction) in accordance with movement of the patient's head.

BRIEF DESCRIPTION OF THE DRAWINGS

The accompanying drawings incorporated in and forming a part of the specification, illustrate several aspects of the present invention, and together with the description serve to explain the principles of the invention. In the drawings.

Figure 1:
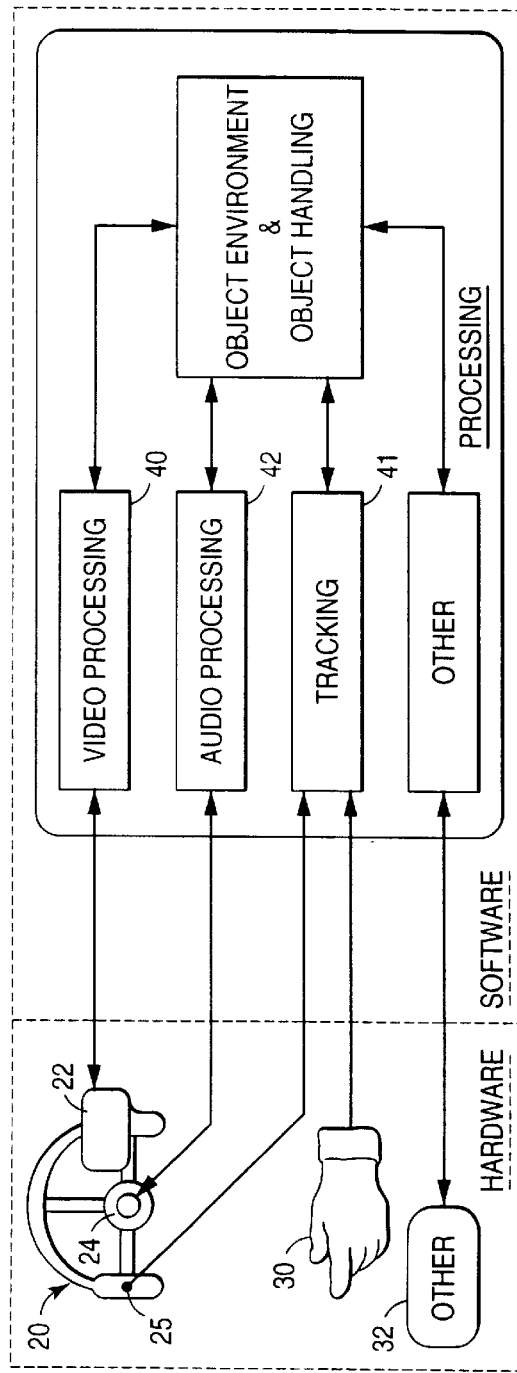
FIG. 1 is a block diagram illustrating the principal hardware and software components in a virtual reality system.

Reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

DETAILED DESCRIPTION OF THE PREFERRED EMBODIMENT

Turning now to the drawings, FIG. 1 illustrates the principal components in a virtual reality system depicting the separation between hardware and software. As will be described in further detail below, the primary aim of the present invention is to provide an effective means for treating a variety of patients suffering from anxiety disorders of various kinds. Because virtual reality systems respond to patient movements to create a sense of presence or "immersion" within the virtual environment, applicants have found that such systems provide an effective vehicle for achieving the concepts of the present invention.

As is known, virtual reality systems operably combine hardware and software in real-time fashion. A central hardware component in almost any virtual system is the headgear 20. Various types of headgear are known. For example, a headgear, such as that illustrated in the figure, has only a single video screen 22 for displaying an image of a virtual environment immediately before the user's eyes. The screen 22 may be flat or, alternatively, curved, either physically or optically, to extend to each side of the eyes and effectively cover much of the user's peripheral vision. Alternatively, stereo goggles may be utilized. Headgear of this type provide two display screens—one immediately in front of each eye. As is known, the images displayed on each screen are slightly offset, so as to provide the appropriate sense of depth perception for objects displayed on the screens.

Speakers 24 may be also be provided in the headset 20. Like the video images displayed on the screen 22, sound may be similarly provided to support the virtual environment illustrated on the video screen. As mentioned, an important feature in a virtual reality system is to provide the user with a sense of presence within the virtual environment. To this end, sensors 25 are provided in connection with the headgear 20 to monitor the position and movement of a user's head. As the user moves his head, the image displayed on the video screen 22 is adjusted accordingly. Similarly, the volume of the sound emitted on speakers 24 may be accordingly adjusted. That is, in the virtual environment, the sound source may be assigned a location. As the user moves his head, the sound volume may be slightly varied between the two speakers to coincide with the alignment of the user's ears with the sound source.

Another hardware component frequently used in a virtual reality system is a device, usually resembling a glove, that is worn on the user's hand. The device is equipped with numerous position and bend sensors to closely monitor finger and hand movements. All such devices will be hereinafter referred to as "sensor-gloves" 30. This device is worn on a user's hand like any normal glove. It is equipped, however, with numerous sensors to monitor the position and movement of the user's hand and fingers, and provides an effective means for allowing the user to positively engage the virtual reality environment as more than a mere observer. It will be appreciated that the visual and audio sensory perceptions provided in connection with the headgear 20 may effectively immerse the user in the virtual environment, as an observer, other mechanisms are required in order to allow the user to interact within the virtual environment. The sensor-glove 30 provides this mechanism.

For example, one of the virtual environments that will be discussed in connection with the present invention, is an elevator used for treating patients with acrophobia (fear of heights). The elevator includes control buttons to allow the user (patient) to instruct the elevator to go up, go down, or stop. These control buttons are visually presented to the user on the display screen of the headgear. They are not physically real, but exist only visually in the virtual environment. The user, nevertheless, is able to interact with that environment and depress the buttons by using a sensor-glove 30, or other similar input means. As the user moves his hand, the system tracks that movement and incorporates an image of the hand into the virtual environment display. Just as in a "real-world" manner, the user may utilize the visual feedback of the display showing the position of a hand in relation to the control buttons to move his hand to align the virtual hand with the control buttons.

Another component, denoted as "other" 32, is provided to illustrate that many other hardware components are known for using virtual reality systems, and may be utilized in connection with the present invention. For example, rather than a video screen 22, provided in a headset 20, an alternative video screen may be provided, such as a CRT positioned in front of the patient. A variety of other input means, other than the sensor-glove 30, are known as well. In this regard, the user may utilize a flight stick, a tracker, a mouse, etc. as a means of providing positive input and interaction with the virtual environment. Indeed, experimentation is presently ongoing in the development of a body suit with numerous sensors to track the movements of a user's entire body, much like the sensor-glove 30 tracks the movements of a user's hand and fingers. An exhaustive description of these devices, however, will not be provided herein, as they will be understood by persons skilled in the art and do not form a part of the present invention.

In conjunction with the various hardware components, software provides the remainder of the virtual environment. In this regard, there are companion processing and interface modules to interact with each hardware component previously described. For example, a video processing module 40 outputs to the display screen 22 the appropriate video information for display to the user. It will be appreciated that this video information reflects not only the environment, but also the position of the user's head as detected by sensors 25 and the position of the user's hand as detected by sensor-glove 30. Similarly, an audio processing module 42 provides similar control over the sound emitted by the speaker 24. Thus, the blocks denoted as "tracking" 41 and "video processing" 42 provide the appropriate input/output interface with the corresponding hardware components. At the same time, these blocks interface (via software) with the virtual (object) environment to integrate the user (via hardware) into the virtual environment.

In regard to the graphical or virtual environment provided by the system and as is known, such virtual reality systems utilize object-oriented programming techniques to effectively provide the virtual environment. In this regard, an object can represent anything that can be named, from something as abstract as degrees of volatility, to something as concrete as a physical object. In addition, objects or parts of programs can inherit features from other objects, or from pre-coded generic examples. In this regard, it may be necessary only to note that one object is identical to another except for a certain feature or features, and then to define the differences.

After designing the various objects that will be used in a given virtual environment, object characteristics must also be defined. These characteristics contain rules of behavior that define how a certain object will act or appear in a given environment. For example, balls bounce in response to gravity and elasticity, water flows at a rate relating to both the depth of the water and the inclination or grade down which the water flows. These dynamics are expressed through algorithms in the software.

In many instances, the definition of particular objects and their associate dynamics is hardware or machine specific. In order to facilitate not only the definition of objects, but also portability among different systems, a variety of commercially-available virtual reality development toolkits have been provided. The identification and description, however, of particular toolkits or other development software is not provided herein, as it is not deemed necessary in order to practice the present invention. Indeed, those skilled in the art will appreciate a variety of development tools for implementing the concepts and teachings of the present invention.

In keeping with the description of the object-oriented software, object trees are utilized in combining or defining related objects. For example, a table may consist of a table top and 4 legs, each of which may be expressed as a separate object. Since each of the 4 table legs is fixed in relation to the table top, a logical relation (fixed) is defined among the five objects. This may be expressed in terms of parent-child objects, wherein the table top is a parent object, and each leg is a child object of the parent. As is know, this may be graphically expressed in terms of an object tree. In one embodiment, the relationship between a parent object and a child object is one of location, orientation, and scale. Another way to express this relationship is to say that a child's position is defined in terms of its parents coordinate system, which is in turn defined as its position in relationship to its parent's coordinate system, and so on. All objects in a tree have a position that is ultimately defined in terms of the coordinate system of the top-most object, or root node. Utilizing object trees, movement of a root node object may be calculated independently, and the movement of all other objects within the tree may be calculated based upon the movement of the root object. As is known, this simplifies the calculations required in displaying a given virtual environment.

As is known, an object's position may be represented internally as a 4×4 matrix which is a composite of a translation, a rotation, and a scale transformation. This matrix may be used to determine the position of each point in an object's geometry, in relation to the object's parent. The translation component determines where a point at an object's origin will be from the parent object. The rotation and scale components determine where the points away from the origin will be in relationship to that origin. It is significant to note that the rotation component is a rotation around the parent object's origin, rather than the object's origin and it is also important to note the changes in position of a parent object cause position changes in its child objects as well. To illustrate this point, and in keeping with the example of the table top and four legs, if the table top is rotated., then the legs will rotate about the origin of the table top, as opposed to their individual component origins.

Objects have a geometric appearance which are preferably designed by polyhedron, polyline, text and light sources. This geometry may be read from an object description file, or may be generated dynamically. A geometry may be defined as a list of primitives, each of which may be a polyhedron, a textured polyhedron, a polyline, text, or a light source. A polyhedron primitive is simply a collection of polygon faces which all use a subset of a list of vertices and normals. A textured polyhedron is a special polyhedron which contains texture vertices information used to map textures to the polygon faces. A polyline primitive is a collection of continuous lines which all use a subset of a list of vertices. A text primitive may be a multi-line block of text which has a location, orientation, and scale in relationship to the object it is a part of. The light source primitive is a light definition. Each visible primitive can have a highlighted material associated with it which, if no highlight geometry is specified, will override the primitive's usual material when the object is being highlighted.

Figure 2:
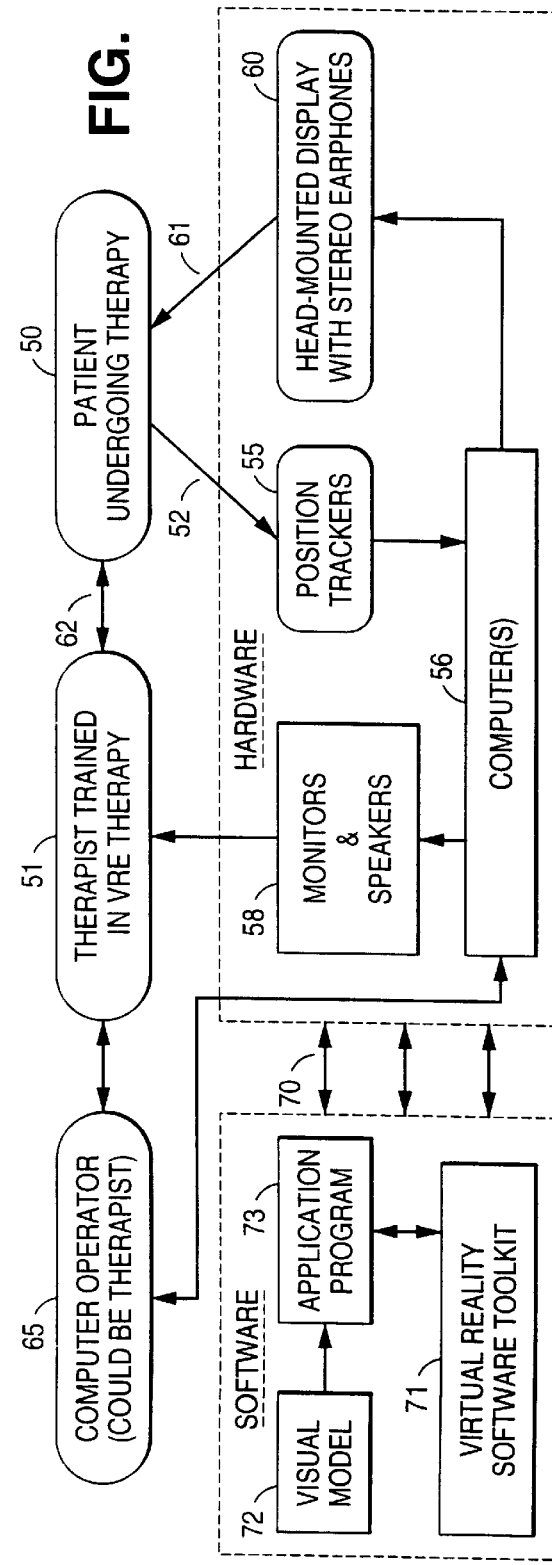
FIG. 2 is a block diagram depicting the interrelation of the principal hardware and software components of a virtual reality system utilized in connection with the present invention.

Having described a generic virtual reality environment for the present invention, reference is now made to FIG. 2, which more specifically illustrates the interrelation of components in a virtual reality system implementing the present invention. In addition to hardware and software, a patient 50 and therapist 51 are also included. Single-ended arrow 52 illustrates the patient interaction with position trackers 55, which may include sensors on the head gear as well as sensors in the sensor-glove 30. This position and sensor data is then input to a computer 56 which controls monitors (video displays) and speakers 58, as well as the head-mounted display 60. The head-mounted display 60, as illustrated by the single-ended arrow 61 provides visual and audio input to the patient 50.

Double-ended arrow 62 reflects bi-directional interaction and communication between the patient 50 and therapist 5 1. In one embodiment, the therapist 51 may, through a series of questions, ascertain the patient's level of anxiety. A computer operator 65 may also be present to provide direct input into the computer 56. The computer operator 65 may be an individual dedicated to control the operation of the computer 56 or, alternatively, may be a therapist with sufficient working knowledge of the computer system to control certain input parameters. For example, and as previously mentioned, one environment of the present invention emulates an elevator for treating patients with a fear of heights. The therapist 51 detects increasing or decreasing, levels of anxiety within the patient 50. Thereafter, the therapist 51, via computer operator, 65 may control the computer 56 to decrease or increase the elevation of the elevator.

Arrows 70 indicate the general interaction between hardware and software. The software is represented in three principle blocks or models: the virtual reality toolkit 71, the visual model 72 and the application program 73. The visual model has the name it implies, defines or depicts the environment for a particular virtual application. The application program receives the visual model and interacts with the virtual reality toolkit so as to define user interaction with the visual model. The operation and interaction of these software modules will be appreciated by those skilled in the art.

Figure 3:
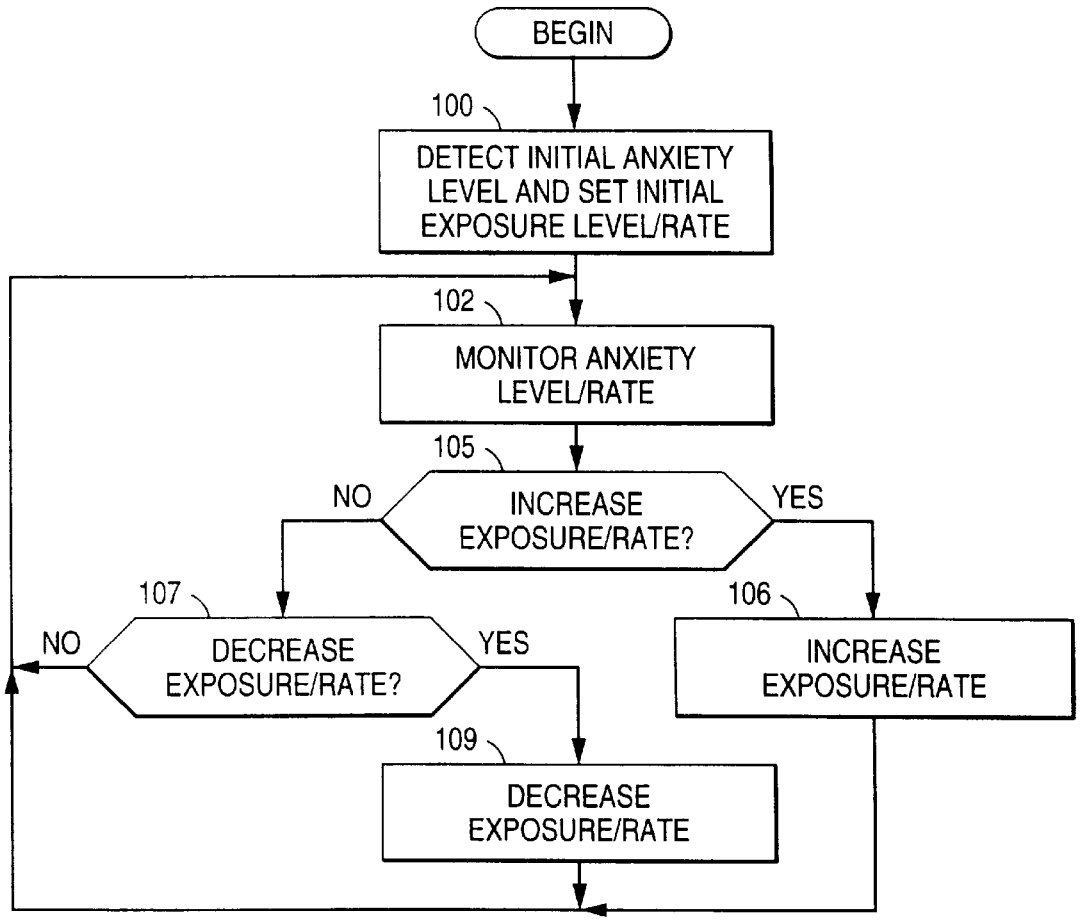
FIG. 3 is a software flowchart illustrating the top-level operation of the present invention.

Turning now to the broad features of the invention, reference is made to FIG. 3, which shows a software flowchart illustrating the principal steps in the present invention. Broadly, the present invention exposes a patient with a particular anxiety disorder to a virtual environment emulating an environment or event targeted to elicit an increase in patient anxiety, associated with a particular anxiety disorder. For example, in patients having a fear of heights, various virtual environments including an elevator, a balcony, and a walking bridge have been designed to elicit patient anxiety. The system operates to vary the intensity of the virtual environment in response to changing levels of patient anxiety. In a treatment method known as graded exposure, a patient is exposed to a particular stimulus that elicits an increased anxiety. After a period of time, with continued exposure, the patient anxiety begins to subside. In response, the system operates to change or intensify the virtual environment in order to again increase patient anxiety. This process is repeated through several gradations as a way of efficiently exposing patients to feared environments or stimuli.

More specifically, the operation of the present invention begins by detecting or otherwise receiving an initial patient anxiety level (Step 100) and setting an initial exposure level or rate accordingly. In this regard, rather than beginning at some default exposure level or rate, a preferred embodiment of the invention recognizes that patients' anxiety levels may be different at the onset. For example, on an initial therapy visit, a first patient may be innately more apprehensive than, for example, a second patient. Similarly, the first patient may have a certain level of anxiety or apprehension on his or her first visit with the therapist, and a lower level of anxiety or apprehension when beginning a treatment session on a subsequent visit to the therapist. In these scenarios, the illustrated embodiment accounts for such variations and sets an initial exposure rate or level accordingly.

As previously mentioned, the system may detect or receive the initial patient anxiety level by data input manually by a therapist and/or computer operator. Alternatively, a sensor may automatically detect a level of patient anxiety. The sensor may be in the form of a device that monitors the patient's pulse rate, blood pressure, or epidermal moisture.

The illustrated embodiment of FIG. 3 also differentiates between exposure level and exposure rate. One or the other may be appropriate for any particular embodiment. In the elevator example previously mentioned, the illustrated embodiment may set the initial exposure level of, for example, the third floor. In this instance, the elevator would ascend to a third floor level and stop. It would remain stopped until the patient anxiety subsided to a level sufficient to permit further elevation of the elevator. Alternatively, the illustrated embodiment may be configured to elevate the elevator at a constant rate. Based upon the patient anxiety, the speed or rate at which the elevator ascends or descends may be controllably varied.

In keeping with the description of FIG. 3, once the initial exposure level or rate has been set, the illustrated embodiment thereafter monitors the patient anxiety level (Step 102). Again, this step may be accomplished by physical indicia observed by a therapist and entered by a computer operator into the system. Alternatively, it may be automatically monitored by way of a sensor, as previously described. At Step 105, the system makes a determination, based upon the patient anxiety level, as to whether to increase or decrease the exposure level or rate. If the patient anxiety level is below a certain, predetermined amount then the exposure intensity is increased at Step 106. Alternatively, the system proceeds to Step 107, which determines whether to decrease the exposure level or rate. In this regard, if the patient anxiety level is above a certain, predetermined amount, the system responds by decreasing the exposure level or rate at Step 109. Otherwise, the exposure level or rate is maintained at a constant. This will be the equivalent of maintaining the elevator at a constant ascending rate or holding at a certain, prescribed floor, as previously described.

Although the illustrated embodiment describes reducing the exposure level or rate if the patient anxiety exceeds a certain level, this may not always be desired. Indeed, in exposure therapy, the exposure level is usually maintained even though the patient's anxiety level is high. The exposure is typically maintained until the patient anxiety begins to subside, and then the exposure is increased. Terminating or reducing exposure while patient anxiety is high may adversely reinforce avoidance or escape. The illustrated embodiment, nevertheless, recognizes that, consistent with the invention, the system may be designed with the flexibility to reduce exposure levels in extreme situations.

It will be appreciated that FIG. 3 illustrates the very broad elements of the present invention, and is not dependent on any particular embodiment or virtual environment. Indeed, specific virtual environments and embodiments will be discussed in connection with FIGS. 4 through 16.

Figure 4:
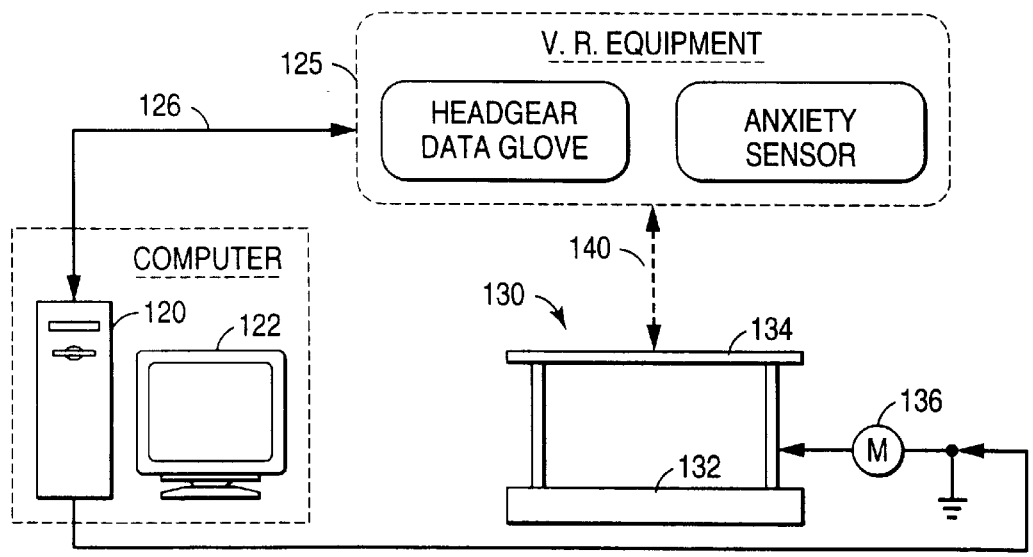
FIG. 4 is a block diagram illustrating the principal hardware components of an embodiment constructed in accordance with one aspect of the present invention.

To better illustrate the present invention by discussing several particular embodiments, reference is now made to FIG. 4. FIG. 4 illustrates the principal hardware components in an elevator embodiment, previously discussed, for use in treating patients having a fear of heights. The system includes a computer 120 containing the virtual environment and for executing the software necessary for implementing the virtual environment. An optional display 122 may also be provided. When included, the display 122 may be used by the therapist as a means of viewing the same visual scene contemporaneously viewed by the patient. That is, the video output by the computer 120 onto the display screen in the headgear worn by the patient, may be simultaneously output to the display 122, where it may be viewed by the therapist 51.

Block 125 generically denotes the virtual reality equipment utilized by the invention, including the headgear 20 (see FIG. 1), the sensor-glove 30, and anxiety sensor previously discussed. Double-ended arrow 126 represents bi-directional communication between the virtual reality equipment 125 and the computer 120. That is, information is communicated from the computer 120 to the headgear, and information is communicated from the sensor-glove and anxiety sensor to the computer 120.

Figure 8A:
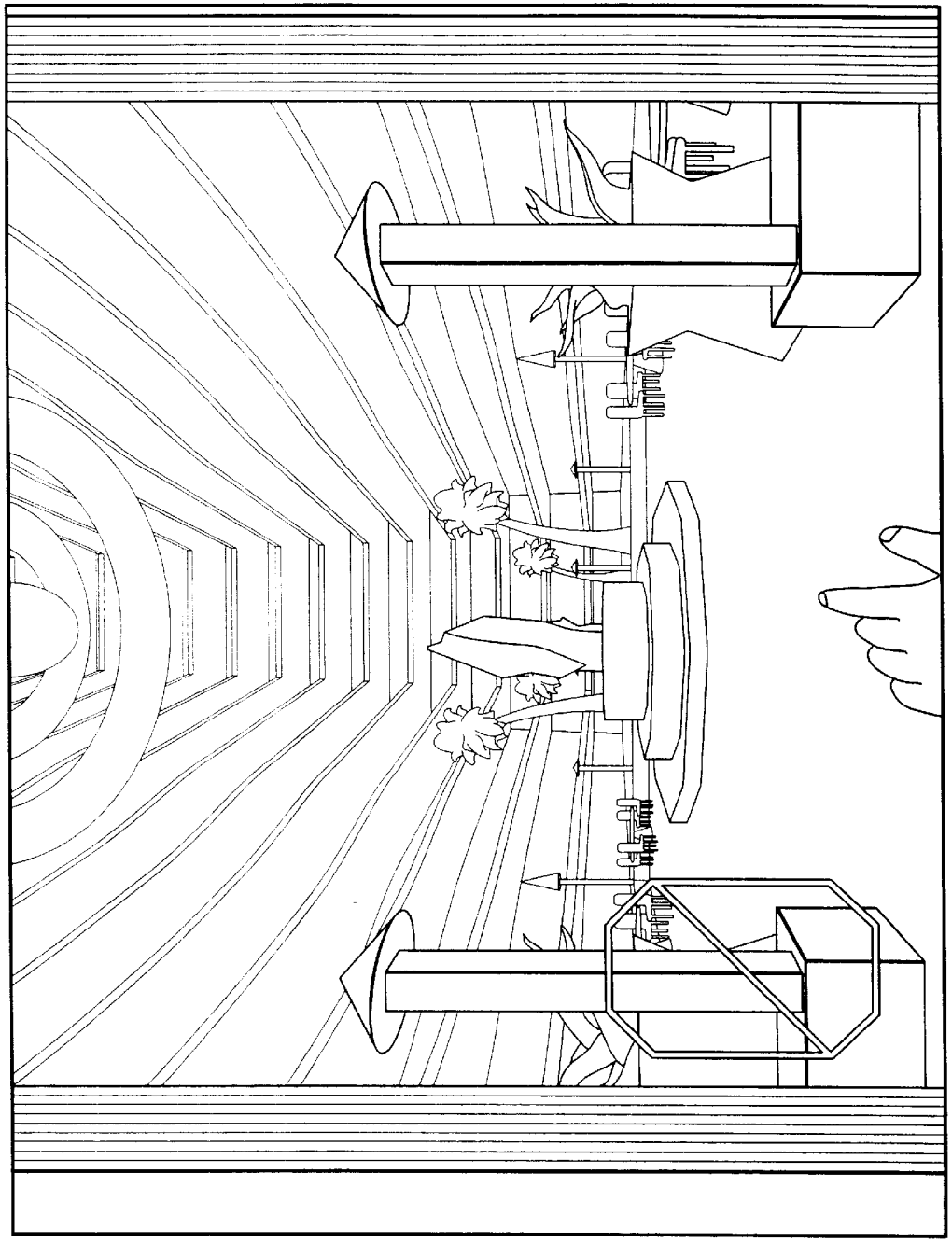
FIGS. 8A–8D are facsimiles of screen displays illustrating a virtual embodiment of one embodiment of the present invention.
Figure 8B:
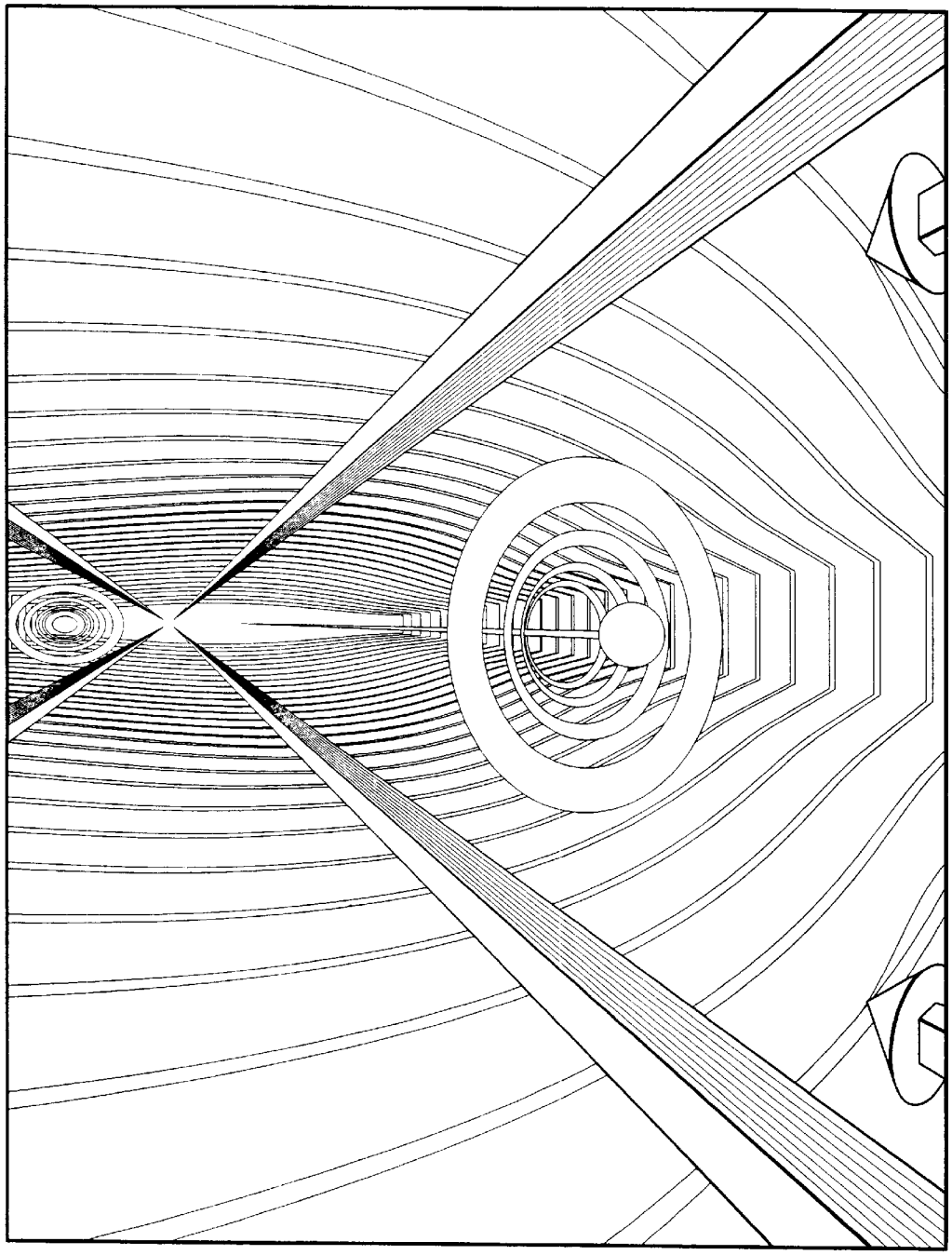
Figure 8C:
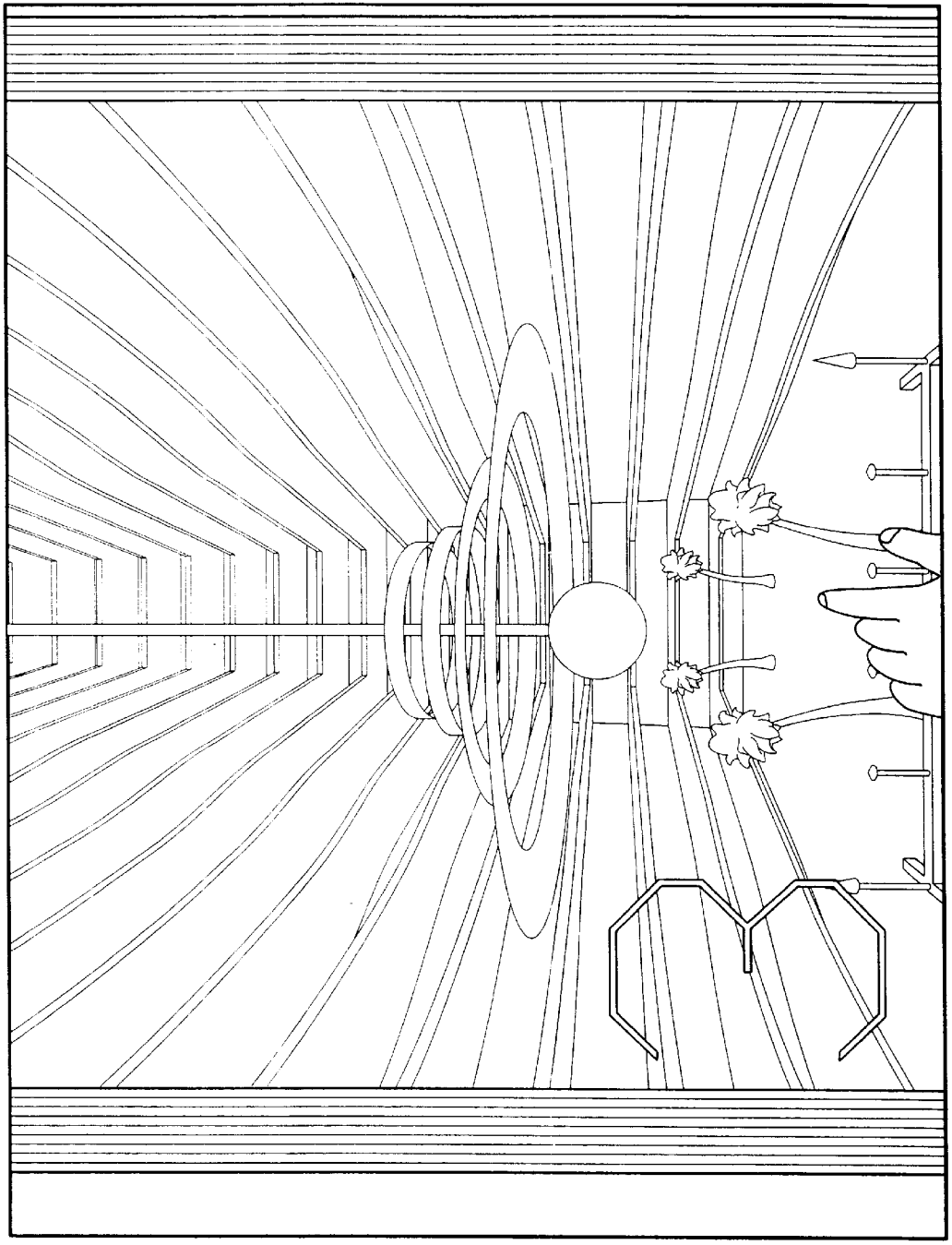
Figure 8D:
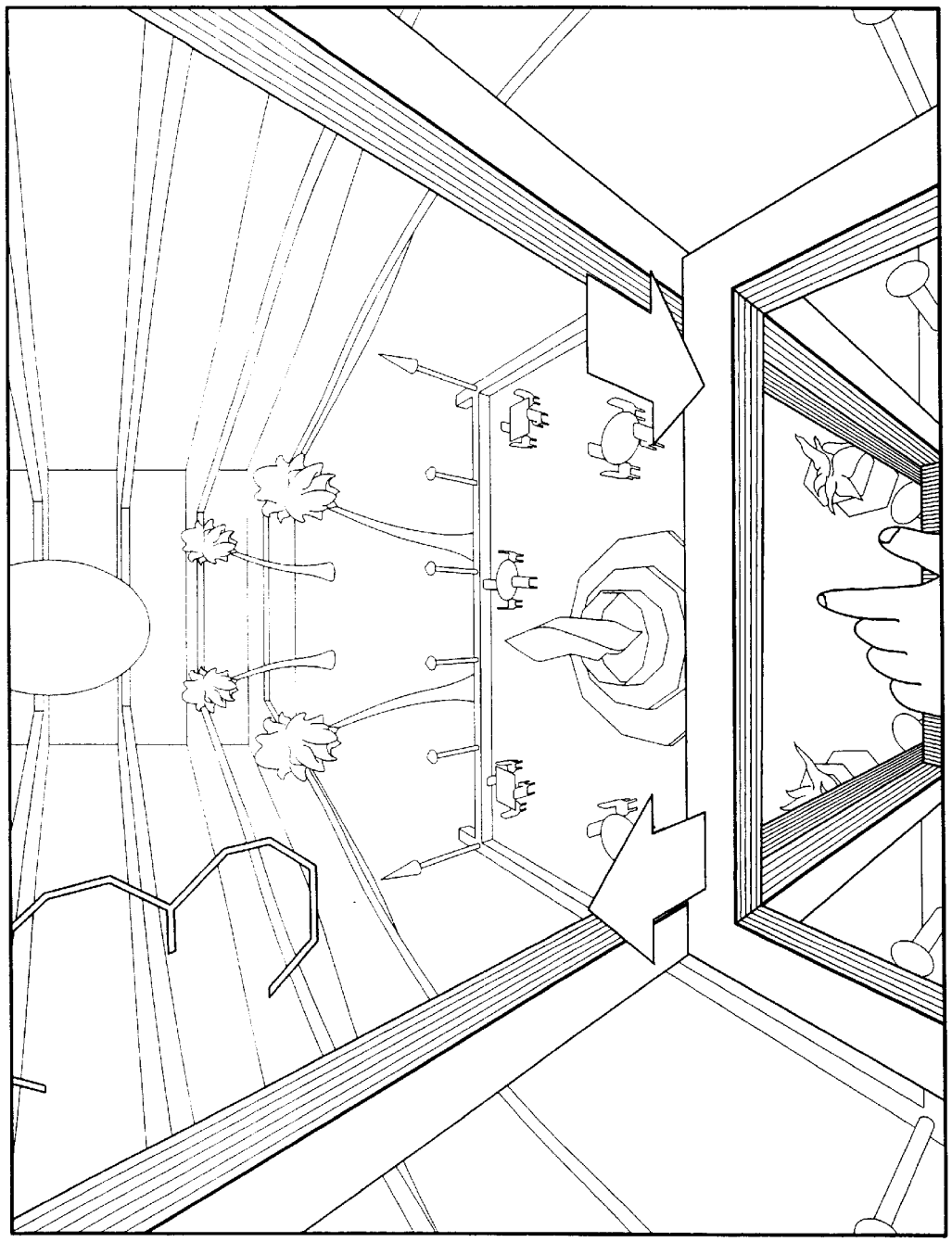

In a preferred embodiment, an elevator platform 130 is provided. The elevator emulated in the virtual environment is an open elevator disposed within a central atrium area of a hotel. In this regard, reference is briefly made to FIGS. 8A–8D, which illustrate various views of this virtual environmental. Specifically, FIG. 8A illustrates a view of the virtual environmental as taken looking outward from the elevator, while the elevator is positioned at ground level. It can be seen that on the ground floor, the environment is depicted as having a plurality of dining tables and an overhanging chandelier. FIG. 8B again illustrates the virtual environment with the elevator positioned at ground level, and with the user looking upwardly. Similarly, FIGS. 8C and 8D illustrate the same virtual environment, with the elevator at an elevated position and the user looking outwardly (FIG. 8C) and downwardly (FIG. 8D). As can be seen, particularly in the downwardly directed view of FIG. 8D, the elevator includes a platform 132 (see FIG. 4) and a handrail 134. The hardware setup as illustrated in FIG. 4 has been configured in connection with the virtual environment so that the physical handrail 134 coincides with the virtual handrail illustrated in the figures. When a user (e.g. patient) is wearing a sensor-glove 30, the system tracks the patient's hand movements so that when the hand wearing the sensor-glove grasps the handrail 134, the image displayed in the virtual environment illustrates the hand grasping the handrail. Similarly, the system tracks the movement of the hand in the vicinity of the handrail or elsewhere so as to coincide with the physical positioning of the user's hand. This provides an element of tactile feedback to the user, particularly when grasping the handrail 134, to further enhance the sense of presence or immersion in the virtual environment and thereby enhance the effectiveness of the exposure therapy.

To further enhance the tactile feedback, a motor 136 may be provided in connection with the elevator platform 130. In this regard, the motor 136 may be disposed to slightly elevate or, alternatively, vibrate the elevator platform 130 in conjunction with a simulated movement of the elevator within the virtual environment. This adds to the sense of movement visually apparent to the user by providing an emulated tactile motion in connection therewith.

The double-ended arrow 140 shown in dashed line illustrates a connection between the elevator platform 130 and the virtual reality equipment 125. This symbolic attachment is realized by a user standing on the platform 130, and wearing the headgear and other virtual reality equipment 125.

Figure 5:
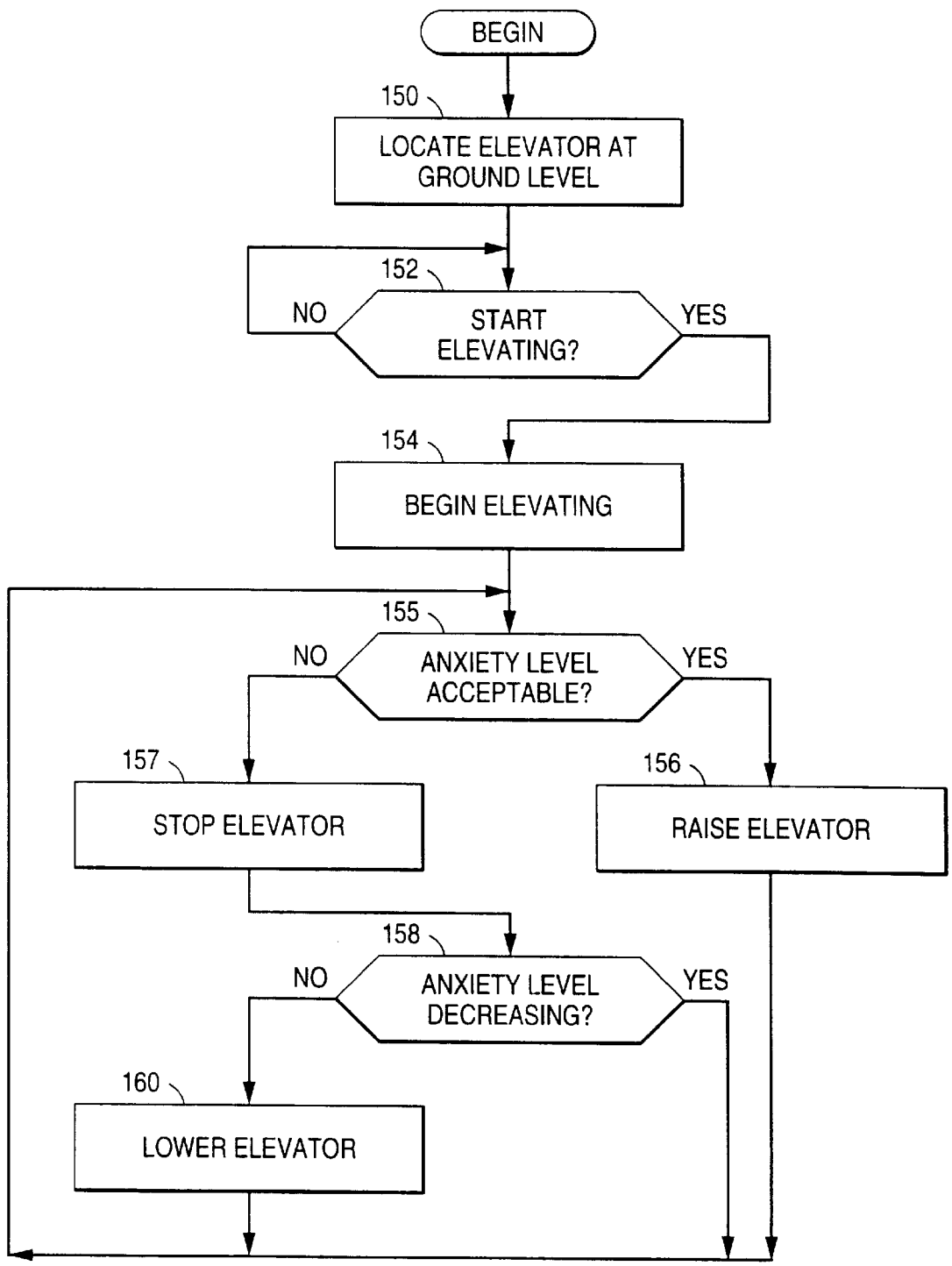
FIG. 5 is a software flowchart illustrating the operation of an embodiment constructed in accordance with one aspect of the present invention.

Turning now to FIG. 5, a flowchart is provided to illustrate the operation of a preferred embodiment of the virtual elevator environment. The system begins the therapy session by locating the elevator at ground level (Step 150). The visual environment as observed by the patient at this level is illustrated in FIG. 8A. In one embodiment, the patient may control the movement of the elevator by using a hand wearing the sensor-glove 30 to depress or activate imaginary control buttons in the virtual elevator. Alternatively, the system may be configured to operate automatically, utilizing anxiety sensors in connection with the elevator control. In this regard, the system may monitor anxiety sensors until the patient's anxiety level is low enough to begin elevating the elevator (Step 152). If, for example, the patient's pulse rate, blood pressure or epidermal moisture level are below certain predetermined amounts, the system begins emulating the elevation of the elevator (Step 154). As the elevator continues upward, the anxiety sensors continue to monitor the patient anxiety level. So long as the anxiety level remains under a certain acceptable level (Step 155), the system would continue to elevate the elevator (Step 156). Once, however, the patient anxiety level exceeds a certain predetermined threshold, the system stops the elevator (Step 157). In the illustrated embodiment, Step 158 checks to see whether the patient anxiety level begins to decrease after the elevator has been stopped. If so, control returns to Step 155 where the patient anxiety level is again tested to determine whether to raise the elevator (Step 156) or maintain the elevator in its halted position (Step 157). If, however, halting the elevator in step 158 does not result in decreased patient anxiety, the system may respond by lowering the elevator (Step 160).

It will be appreciated that, in the foregoing example, the patient anxiety level may be sensed automatically, or may be manually input into the system by the attending therapist. It will be further appreciated that FIG. 5 illustrates only one embodiment of the invention and variations to the particular elevator control may be implemented entirely consistent with the concepts and teachings of the present invention. Indeed, further complexity may be added to the system to account for not only elevation changes in the elevator, but also rate changes in the speed of the elevation or descent of the elevator. In this regard, reference is made to FIG. 6.

Figure 6:
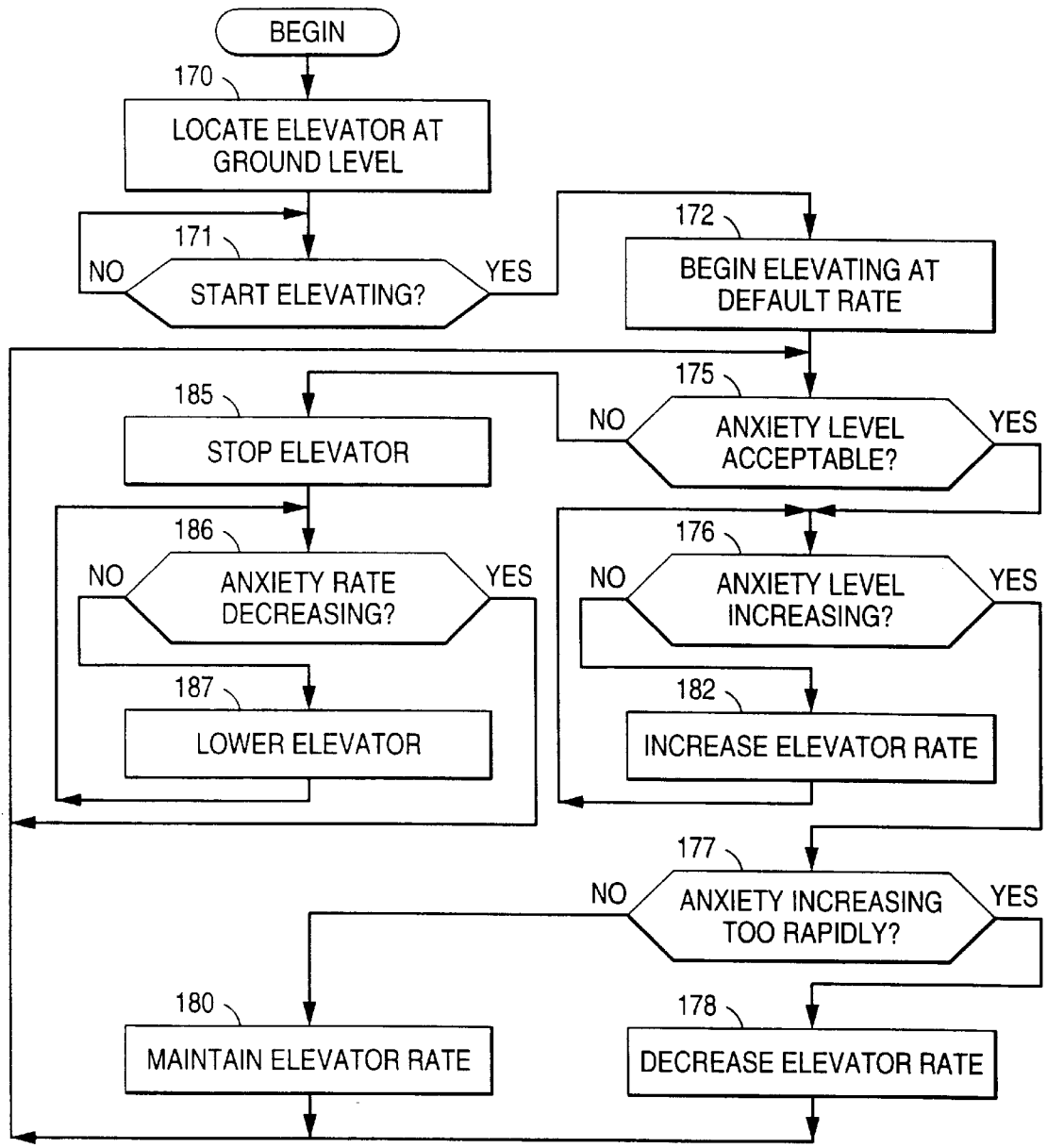
FIG. 6 is a software flowchart illustrating the operation of an embodiment constructed in accordance with one aspect of the present invention.
Figure 7:
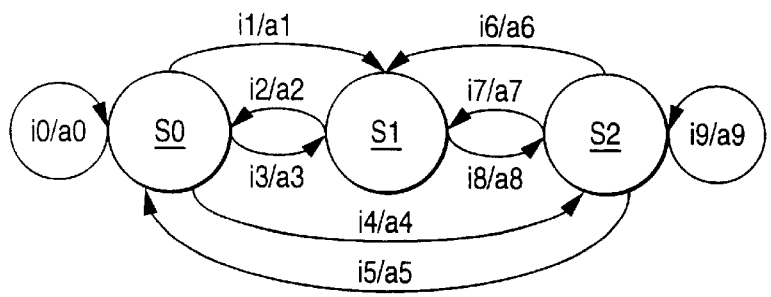
FIG. 7 is a state diagram illustrating the operation of an embodiment constructed in accordance with one aspect of the present invention.

The embodiment illustrated in FIG. 6 also begins by locating the elevator at ground level (Step 170). Thereafter, it assesses the patient's anxiety level either by therapist input or by automatic sensors, in a manner previously described (Step 171). If the patient's anxiety is below a certain level, then the system begins elevating the elevator at a default rate (Step 172). Thereafter, the system monitors the patient anxiety level. If the anxiety level is acceptable (see Step 175), the system may then check to determine the rate at which the anxiety level is changing. If the anxiety level is increasing too rapidly (see Steps 176 and 177), then the system will decrease the rate of elevation (Step 178). If the level of anxiety is increasing, but not increasing too rapidly, then the system may maintain the present elevator rate (Step 180).

If, however, the level of patient anxiety is not increasing (Step 176), then the system may operate to increase the rate at which the elevator is ascending (Step 182). As can be verified from the flowchart, if, at Step 176, the system detects an increasing level of patient anxiety, then the system will either proceed through Step 178 or Step 180. Thereafter, system control returns to Step 175 wherein a check is made to determine whether the level of patient anxiety is acceptable. If not, the system may stop the elevator (Step 185). Then, the system may check (Step 186) to determine whether the level of patient anxiety is decreasing. If so, the system returns to Step 175, and once the level of patient anxiety is again acceptable, the system may begin increasing the rate of elevation. If, however, at Step 186 the system does not detect decreased patient anxiety, then the system may operate to lower the height of the elevator (Step 187).

Again, it should be appreciated that the embodiment depicted in FIGS. 5 and 6 are presented only for purposes of illustrating features of the present invention, and the broader aspects of the invention should not be construed as limited to the embodiments illustrated in these figures.

As previously mentioned, the system may be configured to operate under the control of either the patient, or a computer operator, rather than under the automatic control utilizing anxiety sensors. Under the manually operable scenario, the operation of the system may best be described by reference to the state diagram illustrated in FIG. 7. As illustrated in this figure, there are three states of operation: S0, S1, and S2. When in state S0, the elevator is moving upwardly. When in state S1, the elevator is stopped, and, when in state S2, the elevator is moving downwardly. The lines having arrows indicate a state change. In standard state diagram notation, and as will be understood, associated with each arrow is an input and an output represented by notation iX/aY. In this notation iX represents an input, where X is a number from 0 to 9. Similarly, aY represents an output, where Y is a numeral 0 to 9. Thus, there are 10 inputs and 10 outputs associated with the various state changes. Indeed, Table 1, produced immediately below provides all requisite information for reading and interpreting the state diagram of FIG. 7. The left-hand column of the table lists all states S0 through S2, all inputs i0–i9 and all outputs a0 through a9. The right-hand column of the table provides the corresponding state, input, or output/action taken by the system.

TABLE I

| | |
|---|---|
| S0 | Elevator is moving up |
| S1 | Elevator is stopped |
| S2 | Elevator is moving down |
| i0 | Elevator has not reached the top |
| a0 | Move elevator up (using desired speed) |
| i1 | Elevator has reached top |
| a1 | Stop elevator moving up |
| i2 | Up key/control button is pressed |
| a2 | Start moving elevator up |
| i3 | Stop key/control button is pressed |
| a3 | Stop moving elevator up |
| i4 | Down key/control button is pressed |
| a4 | Start moving elevator down |
| i5 | Up key/control button is pressed |
| a5 | Start moving elevator up |
| i6 | Elevator has reached bottom |
| a6 | Stop moving elevator down |
| i7 | Stop key/control button is pressed |
| a7 | Stop elevator moving down |
| i8 | Down key/control button is pressed |
| a8 | Start moving elevator down |
| i9 | Elevator has not reached bottom |
| a9 | Move elevator down (using desired speed) |

For example, when in state S0, the elevator is moving upwardly. There are two input conditions that can cause the elevator to transition from state S0 (where it is moving upwardly) to State S1 where it is stopped. One of these conditions occurs when the elevator reaches the top of its range of elevation. The second occurs when either the patient or therapist manually controls the system to stop the elevator. The first of these scenarios is represented by i1 (where the elevator has reached the top). The corresponding output a1 instructs the system to stop the elevator from moving upwardly. Similarly, i3 represents the depression of the manual control to stop the elevator from moving upwardly. Corresponding output a3, likewise, stops the elevator from moving upwardly.

In addition to the manipulation of the visual virtual environment as discussed above, the invention may also be configured to provide audible feedback to the user by way of speakers 24. In this regard, the audible feedback may not only provide a sound consistent with the motorized sound or hum of an elevator (that may vary in connection with the varying rate or movement of the elevator), but also may provide additional, environmental noise as well. For example, when the elevator is located at ground level and the visual display is depicting an atrium area of a hotel, it may also be desired to emit the sound of a plurality of personal conversations, for example, emulating the presence of people in the atrium area. This sound may be attenuated as the elevator rises above the atrium level, consistent with sound attenuation in such a real-world scenario.

Figure 9:
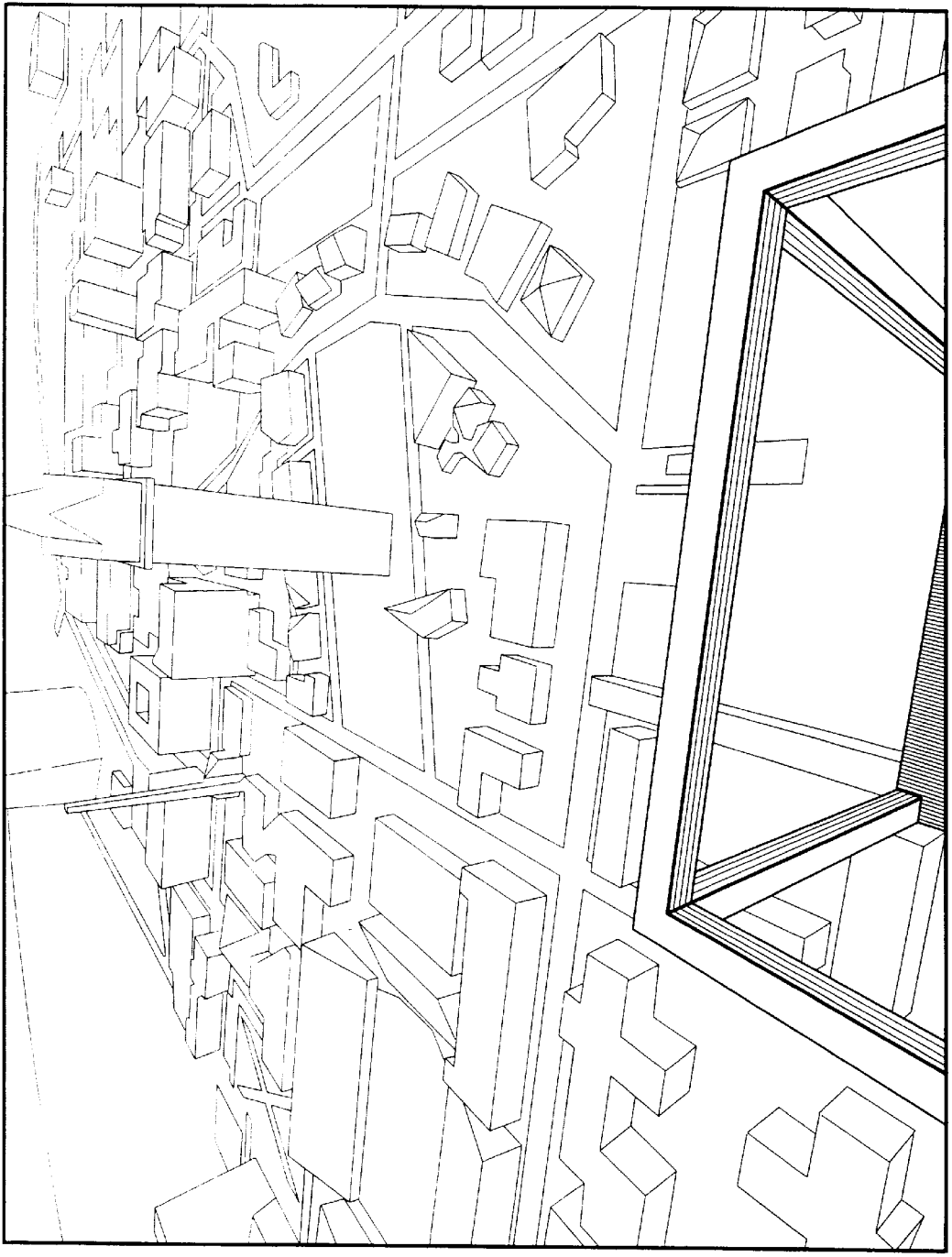
FIG. 9 is a facsimile of a screen display illustrating a virtual embodiment of one embodiment of the present invention.

In addition to the elevator embodiments described above, other embodiments or graphical environments may be provided for treating patients with a fear of heights. One such embodiment is shown in FIG. 9 and includes a view from a balcony. As can be seen in FIG. 9, a balcony handrail is provided like that discussed in connection with the elevator handrail of FIGS. 4 and 8A through 8D. Indeed, the same platform constructed for the elevator embodiment may be utilized in connection with the balcony embodiment. Preferably, a plurality of balcony scenes are provided, each of a varying height. That is, one balcony embodiment may emulate the view from a second or third floor balcony. During an initial treatment session, a patient may be exposed to this environment. Once patient anxiety levels have decreased by virtue of this exposure, the patient may then be exposed to additional balcony scenes of increasing intensity (i.e., higher floors).

Figure 10:
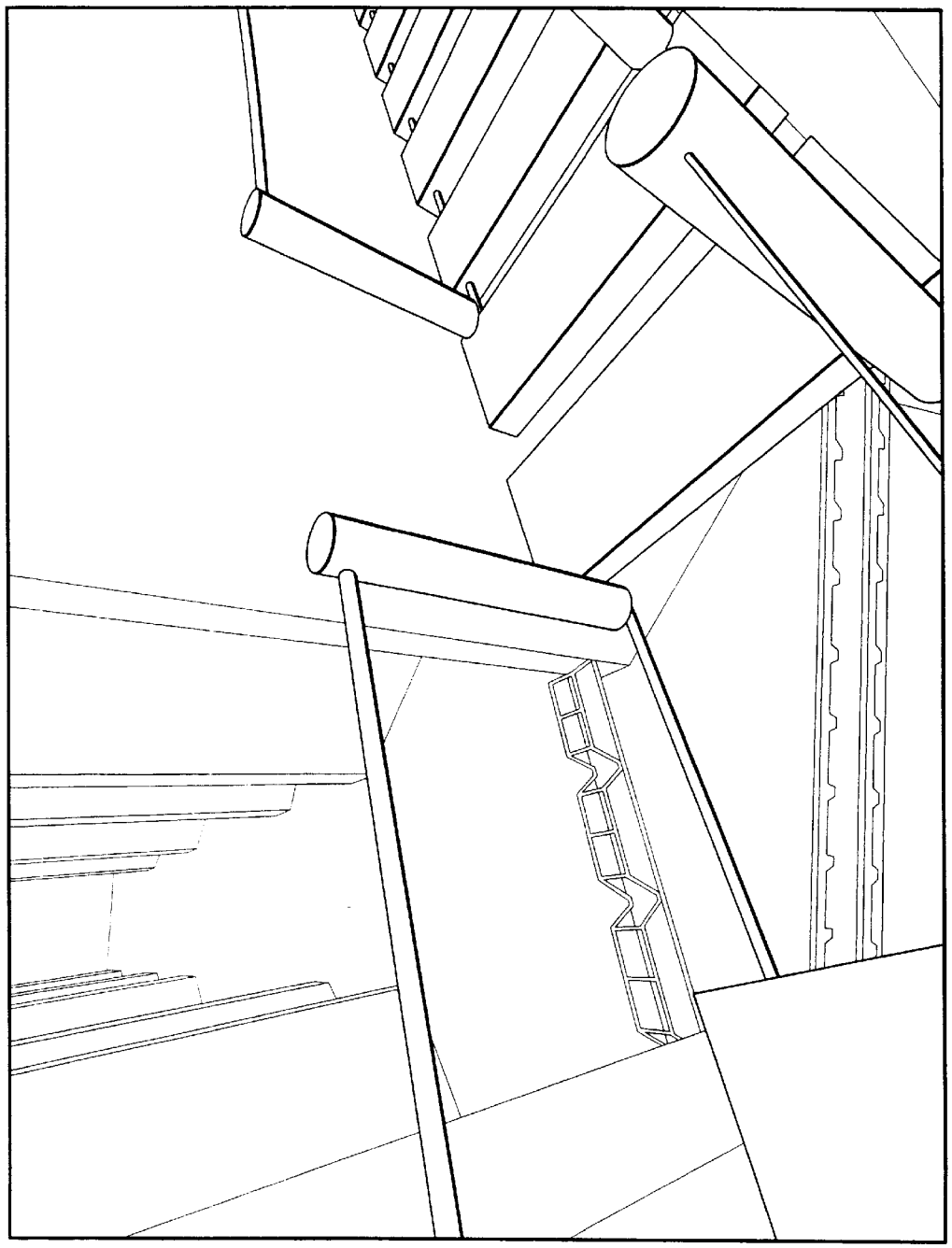
FIG. 10 is a facsimile of a screen display illustrating a virtual embodiment of one embodiment of the present invention.

Yet another embodiment is illustrated in FIG. 10, wherein the virtual environment positions a patient on a suspended, walking bridge spanning a ravine. Depending upon the level of patient anxiety, the system may be adapted to increase the elevation of the suspended bridge or, alternatively, vary the stability of the bridge. In this regard, the system may be configured to provide swaying or other turbulence to a suspended bridge. In such an embodiment, it would be desirable to provide tactile feedback, similar to the elevator handrail, to reinforce the sense of presence or immersion experienced by the patient.

Figure 11:
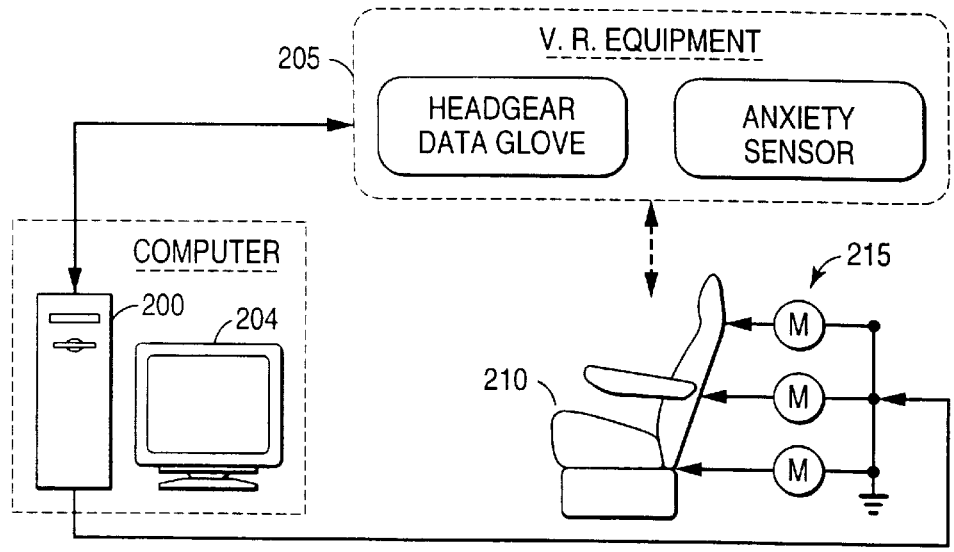
FIG. 11 is a block diagram illustrating the principal hardware components of an embodiment constructed in accordance with one aspect of the present invention.

In addition to utilizing various embodiments of the present invention to provide exposure treatment to patients suffering from acrophobia, the invention is not so limited. Indeed, it is contemplated the invention can be utilized to treat patients having a wide variety of anxiety disorders. The fear of flying is another such example. To be sure, in one embodiment the present invention has been adapted to emulate the interior of a passenger aircraft, from the vantage point of a passenger seat positioned next to a window. Using the headgear, the patient has the freedom and flexibility to observe the virtual surroundings within the aircraft cabin, as well as view a virtual environment outside the aircraft by looking through the window. Like the hardware setup illustrated in FIG. 4, FIG. 11 depicts a similar hardware setup for this embodiment of the present invention. Again, a computer 200 and optional computer monitor 204 are provided to generate and simulate the virtual environment. Virtual reality equipment 205, including the headgear, sensor-glove and anxiety sensor are also provided. Rather than the elevator platform illustrated in FIG. 4, a chair is provided for the patient to sit in. Preferably, this chair closely conforms in size and shape to a typical aircraft seat, to tactily emulate the virtual environment. A plurality of motors 215, responsive to the computer 200, may be provided to further enhance the environment by moving the seat 210. In this regard, a mechanism, such as a motor, may be disposed to tilt the seat forwardly or rearwardly coincident with aircraft landings and takeoffs. Similarly, a mechanism may be provided to tilt the seat from side to side to better emulate turns or aircraft banking. Finally, a mechanism may be provided to generate seat vibrations to better enhance the sense of movement by the patient seated in the chair 210.

Figure 14:
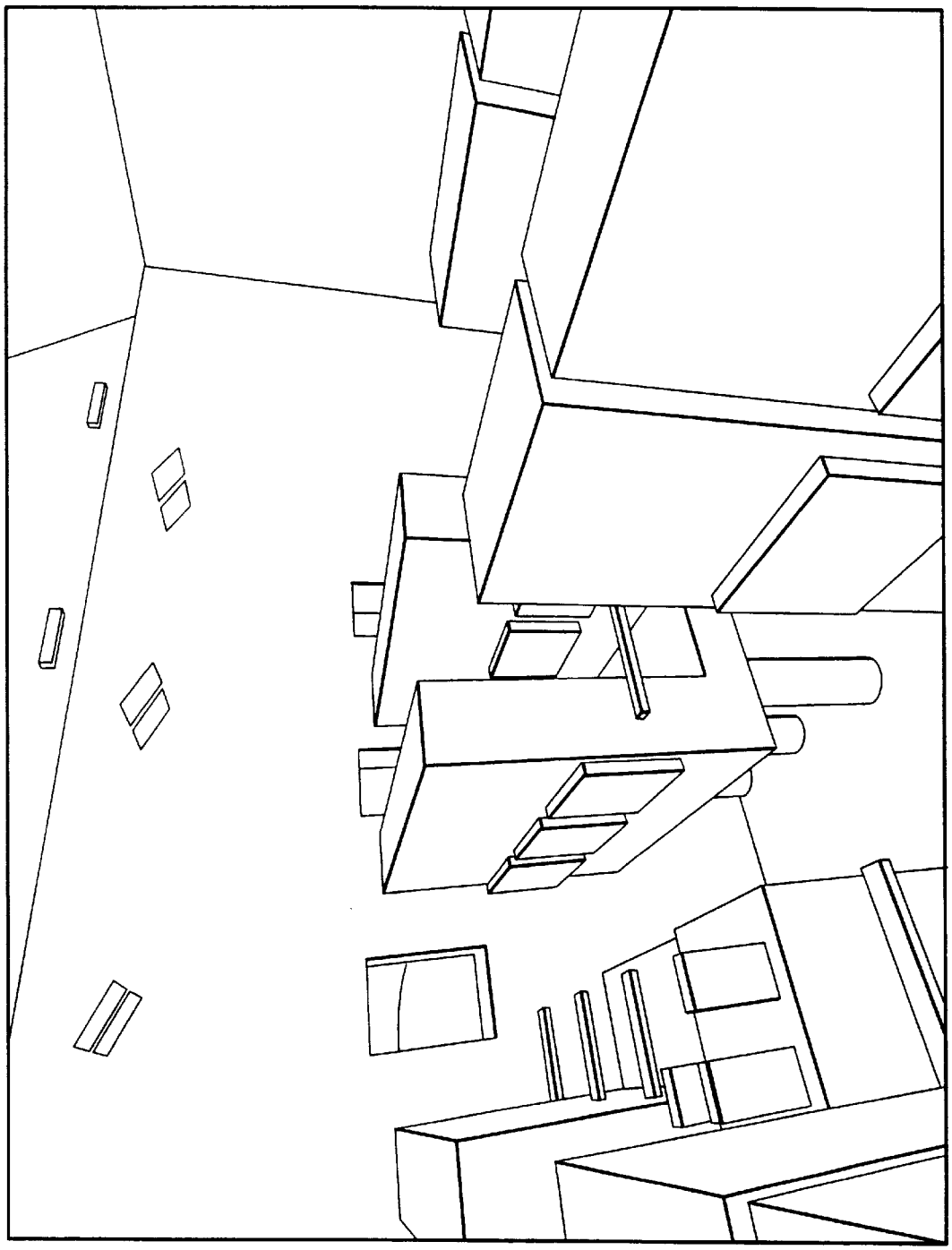
FIG. 14 is a facsimile of a screen display illustrating the interior cabin space of a passenger airplane.
Figure 15:
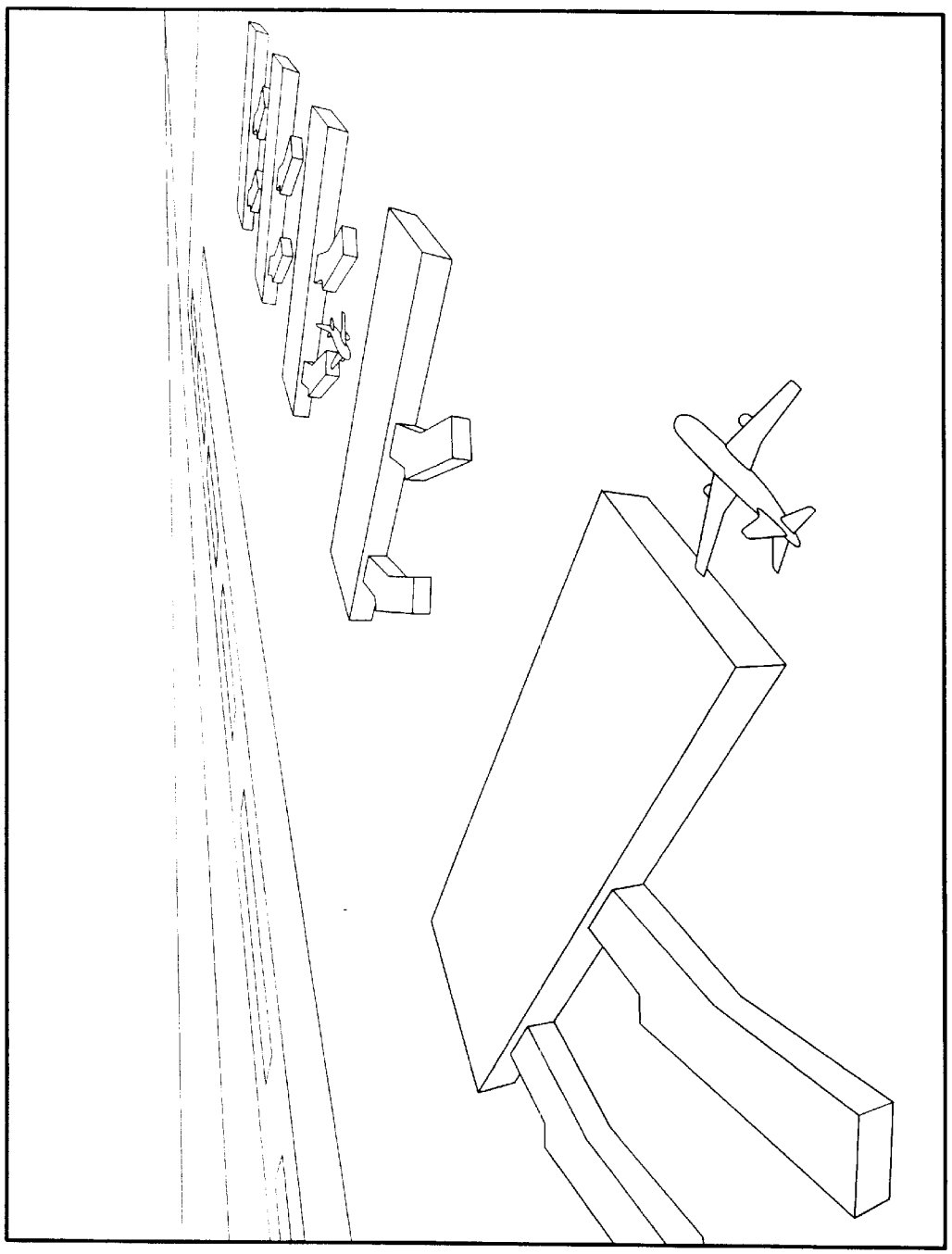
FIG. 15 is a facsimile of a screen display illustrating an airborne view of an airport.
Figure 16:
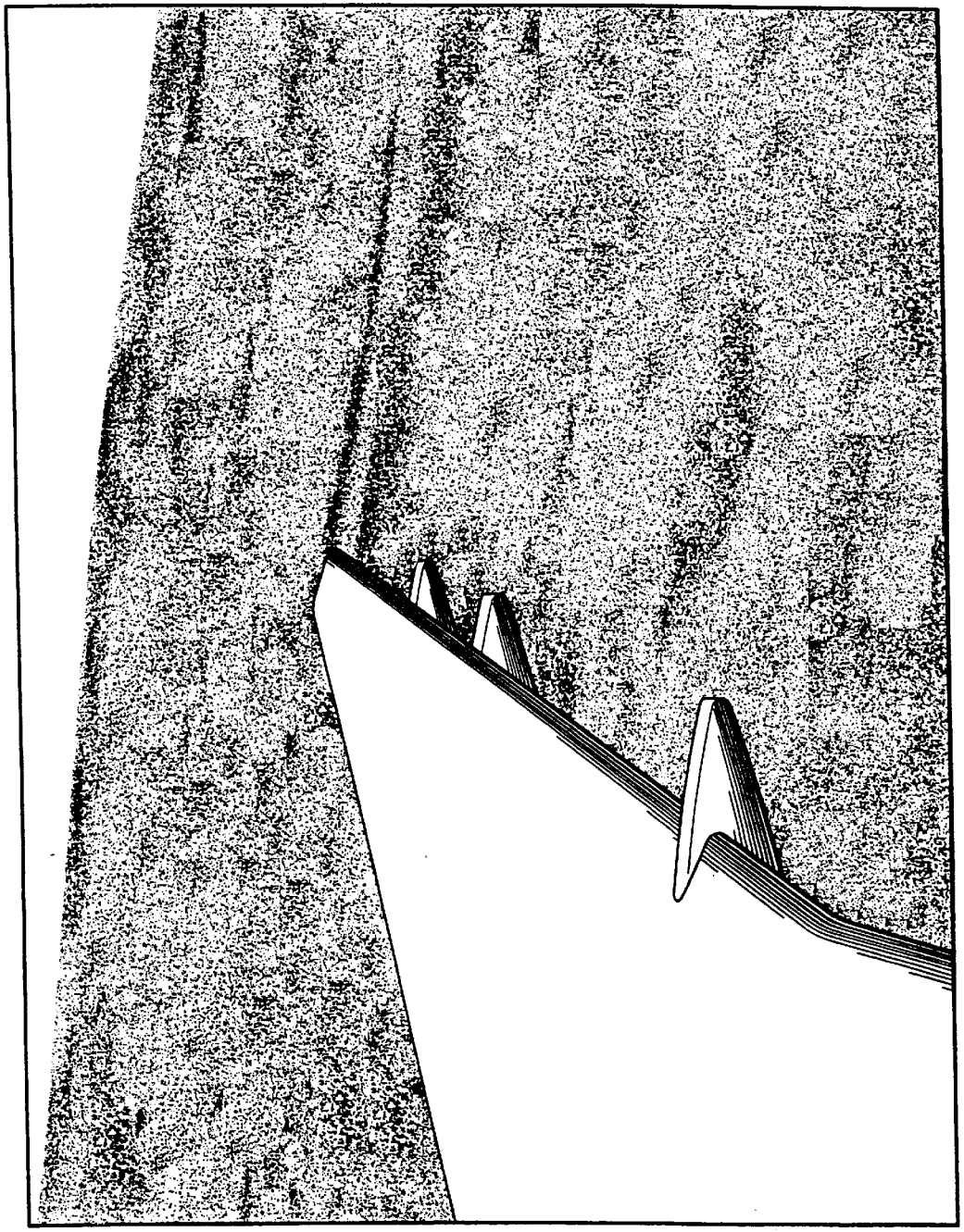
FIG. 16 is a facsimile of a screen display illustrating a view out of a passenger window of an aircraft.

Before proceeding with the description of a preferred software flowchart and state diagram, reference is first made to FIGS. 14 through 16. FIG. 14 illustrates a view of the interior aircraft cabin space as viewed by the patient, seated in a passenger seat. While the aircraft of this embodiment is empty, it may be desired to add the presence of other passengers, flight attendants, etc. to better enhance the sense of presence within the virtual environment. Similarly, corresponding surrounding noise (e.g., conversations) may be emitted via headset speakers 24 to further enhance this embodiment. Likewise, aircraft noise is desirably emitted over the speaker. The noise is controlled to intensify in volume in connection with aircraft takeoff, for example, and a lower volume is emitted coincident with aircraft taxiing.

FIG. 15 illustrates a view of an airport, as observed by looking through the aircraft window. It will be appreciated that the aircraft is airborne when observing the view as illustrated by FIG. 15. Similarly, FIG. 16 illustrates an alternative view out the passenger window, and over an aircraft wing. This view illustrates movement of the aircraft by depicting the ground as blurred in relation to the aircraft wing.

In a presently preferred embodiment, prerecorded video images may be used to provide the view of the exterior of the plane seen through the aircraft window. This allows a high sense of presence to be created while only requiring simulation of the virtual environment of the aircraft interior. This reduces the computational requirements of the system to a level allowing the software to be run on a personal computer, resulting in an enhancement of system performance and a significant cost reduction over the mainframe system which would otherwise be required to generate a three-dimensional simulation of the exterior scenery. Running the simulation on a personal computer based system also allows private clinicians and therapist to operate the system directly, without requiring the aid of computer operations personnel, thereby providing more immediate control of the simulation in response to patient anxiety levels. In an alternative embodiment, the interior of the aircraft may also be simulated by the presentation of prerecorded images of the interior of a real aircraft in a manner responsive to the patient's head position and orientation.

The video images may be played directly from storage on a hard-drive, CDROM, or by streaming over a network, the Internet or other communications system to facilitate remote treatment. Furthermore, the video images may also be encoded in any standard video format, including such examples as MPEG, MPEG2, Quicktime or AVI. The video images may be recorded at a higher resolution than would be possible for a computer generated simulation, and may in fact include recorded images from a real flight, thereby significantly enhancing the realism of the virtual experience. Since the view out of the window includes only objects at a much greater distance from the patient than the interior of the plane, the loss of parallax resulting from displaying a prerecorded video image rather that actually simulating the exterior scenery is negligible.

Another way to significantly improve the realism of the images and increase the sense of presence is to add jitter to the images, simulating the turbulence and small shocks which commonly occur as an aircraft moves on the ground or encounters turbulence in flight. In the preferred embodiment, this jitter may be provided cheaply and with use of little computation power by randomly causing slight changes in the head position coordinates of the patients head in the virtual reality system computations.

It is also possible to replay short looping video streams to simulate continuous conditions such as sitting at the gate or in flight conditions, however it is necessary to include longer video segments to simulate taxiing, take off, landing, and weather transitions. In order to enhance the realism of the experience and increase the presence produced by the virtual reality technology, the transitions between the various video segments which can constitute the external scenery during a therapy session must be as smooth as possible. This smoothness of transition can be accomplished by limiting the transitions to certain set points during the video sequences and by transitioning to a smoothly integrated scene at a predetermined point during the next replay of one of the short repeating loops. The longer sequences will generally only run once, and will automatically transition into the next phase of the simulation.

During the longer video sequences, it may be desirable to include an indicator to inform the therapist whether it is possible to transition to the next sequence at a given time. In the presently preferred embodiment this is indicated by inclusion of an indicator pixel on the monitor view screen. When it is possible to transition, the indicator pixel is illuminated. This pixel need not be present in the virtual environment. Furthermore, it should be obvious that a number of other indicating means are possible.

Figure 12:
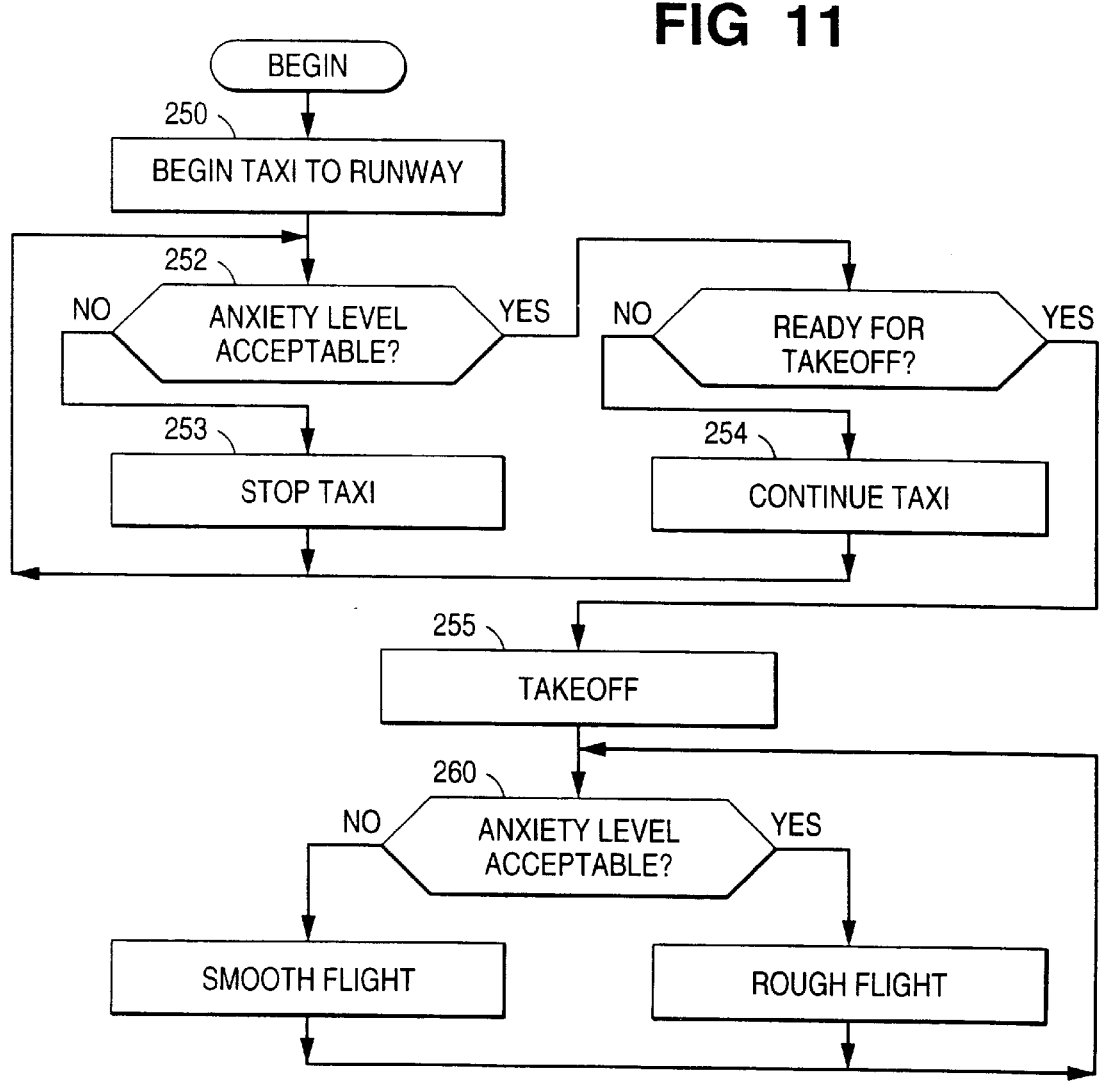
FIG. 12 is a software flowchart illustrating the operation of an embodiment constructed in accordance with one aspect of the present invention.
Figure 13:
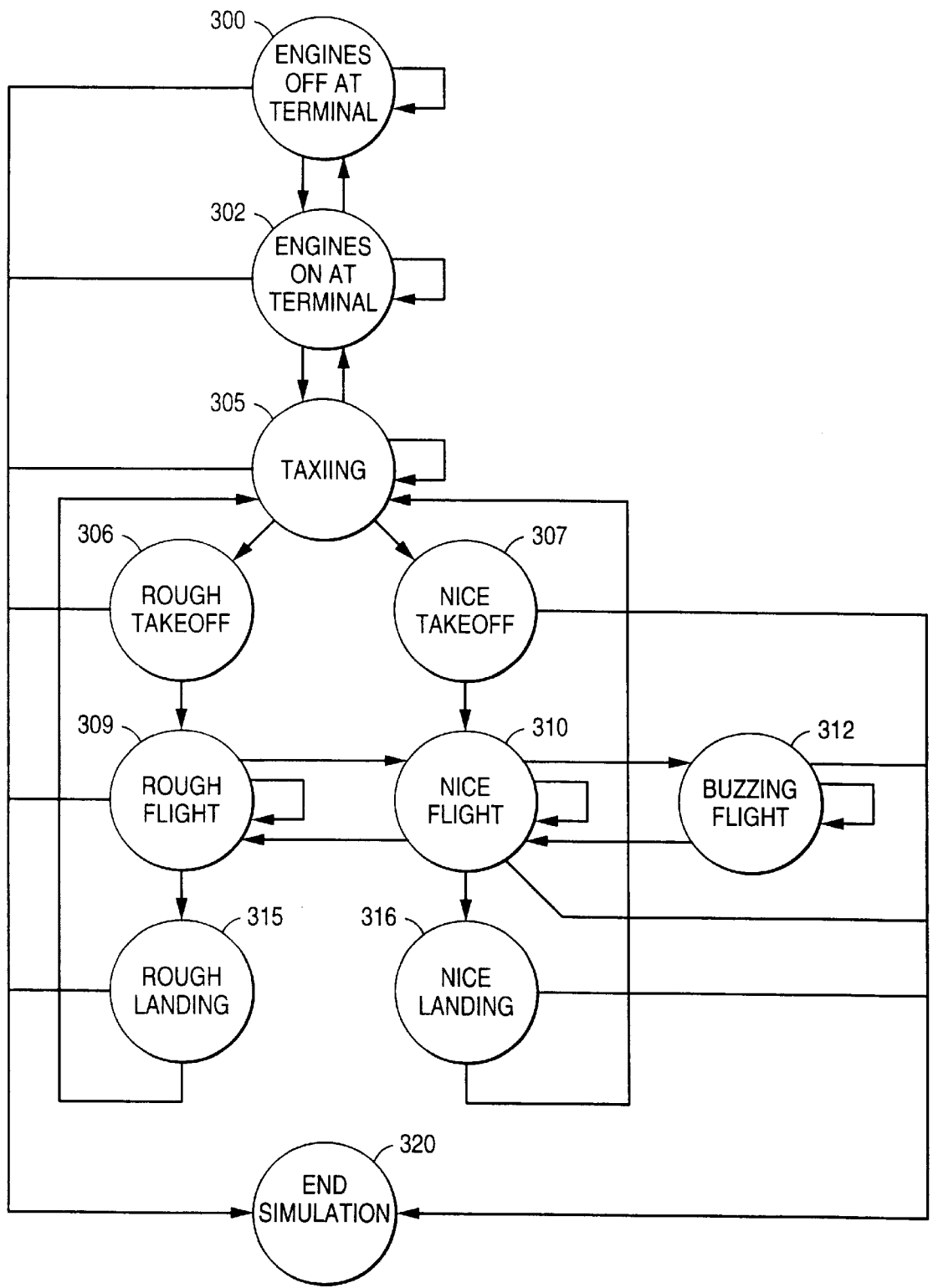
FIG. 13 is a state diagram illustrating the operation of an embodiment constructed in accordance with one aspect of the present invention.

Referring now to FIG. 12, a top-level description of the software operation for this embodiment is depicted and FIG. 13, which shows a state diagram illustrating the various states, and state transitions of the above-described embodiment. Preferably, a therapy session begins with the aircraft at state 300 sitting at the gate of an airport in preparation for departure with the engines off. During this phase of the simulated flight, a short video loop simulating the exterior scenery is played. Accompanying sound files including low level background noise and music are played in conjunction with the repeating video sequence. Upon command by the therapist or patient, or input from the anxiety sensors the system transitions to the next state 302, simulating sitting at the gate of an airport in preparation for departure with the engines on by simply activating a sound file simulating the engine noise. This state may be maintained until the therapist commands transition to the next state or, alternatively may be maintained for a predetermined time before automatically transitioning to the next state.

The next state 304 is that of taxiing from the terminal to the runway (Step 250). During this phase of the flight, a longer video sequence simulating the external scenery as the plane moves from the gate is first displayed, followed by entry into state 306, which includes a looping video sequence in which the aircraft circles about the runway. When the aircraft has taxied for a sufficient time, the therapist can cause the exterior scenery to transition to state 308 wherein a short repeating video sequence is displayed simulating a stationary scene as the plane sits at the runway in preparation of takeoff. These video sequence are accompanied by sound files including both stationary and moving engine noise along with a low level of background noise.

Not only is this an effective way of gradually introducing the patient into the feared, airborne environment, but also presents a more realistic approach to exposure therapy, since preflight taxiing is always a part of the flight experience. During the taxiing, the patient's anxiety level may be monitored to determine whether the exposure of the therapy session should be taken to the next level (Step 252). If the patient's anxiety level exceeds a predetermined threshold level, then the illustrated embodiment stops the taxiing (Step 253), until the patient's anxiety returns to an acceptable level. If, however, the patient's anxiety level is below a predetermined threshold level, then the virtual emulation continues with the preflight process. That is, if the plane has not yet reached the runway, it continues to taxi (Step 254). If, however, the plane has reached the runway, then the aircraft proceeds to the runway in preparation for take off (Step 255).

When the therapist signals the system to proceed with takeoff, the video sequence transitions to state 310, wherein a longer video sequence is displayed of the external scenery during takeoff and the initial portion of an ascent. During the takeoff, audio files are played including the a speech by the stewardess concerning in flight safety procedures, the distinctive "chime" heard as a plane prepares for takeoff. The simulation also includes an audio file producing the distinct change in engine noise associated with a typical flight takeoff and the distinctive sound produced by retraction of a plane's landing gear. Motors 215, or alternatively a subwoofer speaker, may be controlled to increase the seat vibrations, and the virtual environment, as viewed through the passenger window, illustrates the acceleration and increased velocity of the aircraft proceeding down the runway. Once an appropriate velocity has been reached, the system operates to tilt the seat rearwardly and control the environment out the passenger window to reflect increased aircraft altitude. It will be appreciated that during this time the system continues to monitor the patient anxiety, and if the patient anxiety exceeds a predetermined threshold, the system may abort the simulation.

Preferably, however, the takeoff proceeding will continue until the plane reaches a certain prescribed altitude. Once the cruising altitude has been reached, the system transitions to state 312 initiating a short video sequence simulating clouds passing by the exterior of the plane during a steady flight under good conditions and associated audio files including the steady sound of in flight engines. The system continues to monitor patient anxiety (Step 260). With increased levels of patient anxiety, the system may respond by simulating very smooth flight conditions. In this regard, the speaker emits a fairly constant hum to correspond to smoothly running engines, and a very gentle, regular vibration is provided by the motors 215 to the seat 210.

With reduced levels of patient anxiety, however, the system is preferably adapted to simulate rougher flights. When a rougher flight has been selected, the external scenery sequence smoothly enters transition state 314. State 314 includes a short video sequence simulating passage through a cloud bank and thereby providing a smooth transition from the repeating good weather loop to another short looping sequence presenting a view of darker storm clouds displayed during the bad weather state 316. The audio files associated with the rough flight sequence include the in flight engines, a bell chime indicating the need to fasten seat belts, the crack of lightning and the rumble of thunder.

Additionally, the amount of apparent jitter of the system is increased during the rough flight sequence by increasing the random perturbations to the patient's head coordinates as previously described. Motors 215 may also be controlled to deliver sudden jolts to the seat 210 with corresponding perturbations reflected in the video display. The speakers may also be controllably varied to emit sound variations coincident with these disruptions, to simulate the aircraft hitting air pockets or encountering turbulence.

When the therapist determines that the rough weather state 316 has been maintained for a long enough time, a second transition state 318 may be initiated, again displaying video sequence depicting a transitory passage through a cloud bank followed by a smooth transition back to the good weather state 312.

When the therapist determines that the flight simulation has proceeded for a sufficient length of time, he or she may activate the system to initiate the landing sequence. The landing sequence includes two longer video sequences including an approach sequence as the plane nears the airport and an actual landing sequence. State 320, the approach sequence state includes a view as the plane passes by a city while descending and approaching the airport, and is associated with audio files including the sounds of the seat belt warning chime and the characteristic thump associated with deployment of the landing gear of an aircraft. From state 320, the system may transition back into state 312 to simulate a missed landing approach or low altitude pass over the airport (buzzing flight) or may proceed to state 322.

State 322, the landing sequence provides an external view of the scenery as the plane actually proceeds through final approach and landing and includes audio files simulating the thump of landing, tire skids and the characteristic engine noises associated with thrust reversal and breaking of an aircraft. Of note, significant jitter may be added to simulate the bumps and shocks associated with the initial contact of the aircraft with the surface of the runway.

Following the landing sequence, a short repeating video loop is entered displaying the external scenery while the plane is in state 324, at rest at the end of the runway. From here the therapist may choose to end the simulation, or may select transition to state 326, including a video sequence simulating taxiing back to the takeoff position and may restart the takeoff sequence to simulate another flight. It should be noted that, in addition to stopping the simulation after a successful landing sequence, the therapist may abort the simulation at any point during the therapy session. Furthermore, in automatic mode the simulation may be automatically terminated if at any time the patient anxiety level exceeds a predetermined threshold.

It should be recognized that in variations of the above presently preferred embodiment that simulation may be controlled by the therapist, the patient or automatically by the use of anxiety sensors. Furthermore, the capability exists for therapist based control of the simulation from a remote location utilizing a network, Internet or modem connection. In such a remote therapist controlled embodiment it is also necessary that information about the patient's level of anxiety, either as detected by a sensor or verbally described by a patient, be relayed to the therapist.

In addition to those embodiments depicted in the drawings and previously described, it will be appreciated that the present invention may be utilized in connection with the treatment of other anxiety disorders as well. For example, the present invention may be used in connection with the treatment of patients suffering from post-traumatic stress disorder. It is well documented that many U.S. military veterans, who have served in combat, suffer from post-traumatic stress disorder (or PTSD). Accordingly, exposure therapy by way of virtual environments may be utilized in the treatment of such patients. Clinical reports have indicated that often the highest levels of anxiety of post-traumatic stress disorder patients are exhibited in connection with the memory of being transported by helicopter into combat. Often these memories and the associated anxiety are triggered merely by the sound of a helicopter flying overhead. Therefore, a virtual environment adapted to treat post-traumatic disorder patients may be created to emulate the following scenario. Initially, merely the sound of a distant helicopter is emitted over a speaker. This sound may grow in intensity and volume, so long as the patient maintains safe and appropriate levels of anxiety. As the sound is controlled to intensify, a visual image of the helicopter, first small and then growing in size, may be displayed on the display screen before the patient.

The environment is further controlled to emulate the approach of the helicopter, which is controlled to land in front of the patient. The patient then boards the helicopter which is controlled to take off and fly over jungle terrain, emulating that of Vietnamese combat territory including muzzle flashes and simulations of tracer bullet fire, for example, or any other appropriate territory for a given patient. During this time, the sound of the rotary helicopter blades are audible throughout the emulation, and the patient may be seated in a seat configured to vibrate much like that discussed in connection with the previous, flight embodiment. Other auditory stimuli which presented during the simulation include battle sounds such as guns firing, missiles firing, explosions, radio chatter, and people yelling and screaming.

If, at any time, the patient anxiety level exceeds a predetermined level, the virtual environment is configured and controlled to respond accordingly. For example, if a patient exhibits undue anxiety as the helicopter is making its initial approach to the patient, the system may merely control the helicopter to fly off in another direction. Once the patient's anxiety subsides, another helicopter may then be brought into the environment to approach the patient.

Embodiments of the present invention have also been identified for use in treating other PTSD sufferers. In such embodiments, the sufferers may be exposed to a virtual environment that closely emulates the environment in which their trauma occurred (e.g., driving for motor vehicle accident survivors, assailant for rape survivors, etc.). Similarly, variants of the present invention may be utilized in patients suffering from obsessive-compulsive disorder, by exposing them to environments that would otherwise trigger compulsive urges.

It will be appreciated that the particular embodiment or environment may preferably be tailored to specific patient needs. It will be further appreciated that the treatment methods discussed herein are much more efficient and cost effective for treating patients than actual exposure methods. That is, in connection with patients having a fear of flying, the emulated aircraft environment is much more cost effective than actually having to purchase aircraft tickets or flight time from a private charter. In addition, staying within the confines of the therapist's office, patient confidentiality is maintained. Moreover, potential patient embarrassment by having anxiety attacks in a public place are eliminated. Furthermore, unlike a real scenario, if it is clinically warranted, the exposure session may be immediately terminated. It is well appreciated that such an option is not available in a real-world exposure session.

The foregoing description has been presented for purposes of illustration and description. It is not intended to be exhaustive or to limit the invention to the precise forms disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. A virtual reality system for treating patients having a fear of flying, said system comprising:
    a display for displaying a graphical environment emulating the interior of an airplane, said graphical environment including a window;
    a storage device for storing a plurality of prerecorded video sequences, said prerecorded video sequences being representative of standardized environmental scenarios corresponding to views through an airplane window during different phases of the flight of an airplane;
    a head position sensor for detecting the position of a patients head and generating position signals corresponding to the position of the patient's head; and
    a computer responsive to said position signals for controlling the display of the graphical environment by the display in response to said position signal;
    wherein said computer may retrieve one of said prerecorded video sequences and present said prerecorded video sequence within said window of said graphical environment to simulate a view through said window during said particular phase of flight.

2. The virtual reality system of claim 1, wherein said prerecorded video sequence includes images of scenery recorded through the window of a real aircraft during a particular state.

3. The virtual reality system of claim 1, wherein said prerecorded video sequence is repeated to simulate a continuous state thereby allowing simulation of particular phase of flight for an indefinite period of time.

4. The virtual reality system of claim 3, wherein a smooth transition to a second particular simulated phase of flight is accomplished by replacing said repeating prerecorded video sequence with a second prerecorded video sequence displaying the view during the second particular phase of flight at a specific time during said repeating prerecorded video sequence.

5. The virtual reality system of claim 2, further including an indicator for indicating to a therapist when it is possible to transition from a first prerecorded video sequence to a second prerecorded video sequence.

6. The virtual reality system of claim 1, further comprising a speaker for delivering sound, the sound being logically related to the graphical environment.

7. The virtual reality system of claim 6, further comprising a prerecorded audio sequence which is played through said speaker in conjunction with said prerecorded video sequence.

8. The virtual reality system of claim 2, wherein jitter is induced into said graphical environment in conjunction to pre-selected events during said prerecorded video sequence.

9. The virtual reality system of claim 8, wherein said jitter is induced by varying the head position coordinates processed by said computer.

10. The virtual reality system of claim 8, wherein said jitter is induced during the particular state by randomly varying the head position coordinates processed by said computer.

11. The virtual reality system of claim 6, wherein said speaker includes a sub-woofer mounted under a chair.

12. The virtual reality system of claim 1, wherein said pre-recorded video sequence is adapted such that a portion of the video sequence provides a smooth transition to a portion of a second pre-recorded video sequence.

13. A computer program embodied on a computer readable medium for treating patients with fear of flying comprising:
    a means for receiving data detailing the position of a body portion of a patient;
    a means for storing a prerecorded video sequence representative of scenery which would be visible from an aircraft window; and
    a means for generating a simulated graphical environment responsive to the data detailing the position of a body portion of a patient, said simulated graphical environment including:
        a three dimensionally rendered view of the interior of an aircraft, said three dimensionally rendered view including a window; and
        wherein said prerecorded video sequence may be presented within said window of said three dimensionally rendered view to simulate the view through an aircraft window; and
        a means for outputting data encoding the generated simulation of a graphical environment to a display for presentation to the patient.

14. The computer program embodied on a computer readable medium for treating patients with fear of flying of claim 13, further comprising a means for altering the data detailing the position of a body portion of a patient to introduce apparent jitter into the generated simulation of a graphical environment.

15. The computer program embodied on a computer readable medium for treating patients with fear of flying of claim 14, wherein said jitter is randomly generated.

16. The computer program embodied on a computer readable medium for treating patients with fear of flying of claim 14, wherein said jitter is generated to correspond with specific events in the simulation.

17. The computer program embodied on a computer readable medium for treating patients with fear of flying of claim 13, wherein said prerecorded video sequence includes a video sequence from an actual flight.

18. The computer program embodied on a computer readable medium for treating patients with fear of flying of claim 17, wherein said prerecorded video sequence is adapted such that a portion of the prerecorded video sequence provides a smooth transition to a portion of another video sequence.

* * * * *